US010441366B2

(12) United States Patent
Tabandeh et al.

(10) Patent No.: US 10,441,366 B2
(45) Date of Patent: Oct. 15, 2019

(54) ACTIVELY CONTROLLED OPTICAL TRACKER WITH A ROBOT

(71) Applicant: THINK SURGICAL, INC., Fremont, CA (US)

(72) Inventors: Saleh Tabandeh, Fremont, CA (US); Joel Zuhars, Fremont, CA (US); Daniel Patrick Bonny, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 282 days.

(21) Appl. No.: 15/505,205

(22) PCT Filed: Oct. 22, 2015

(86) PCT No.: PCT/US2015/056940
§ 371 (c)(1),
(2) Date: Feb. 20, 2017

(87) PCT Pub. No.: WO2016/114834
PCT Pub. Date: Jul. 21, 2016

(65) Prior Publication Data
US 2017/0245946 A1    Aug. 31, 2017

Related U.S. Application Data

(60) Provisional application No. 62/161,693, filed on May 14, 2015, provisional application No. 62/067,001, filed on Oct. 22, 2014.

(51) Int. Cl.
*A61B 34/20* (2016.01)
*A61B 34/30* (2016.01)
(Continued)

(52) U.S. Cl.
CPC ............. *A61B 34/20* (2016.02); *A61B 34/30* (2016.02); *A61B 34/32* (2016.02); *A61B 90/37* (2016.02);
(Continued)

(58) Field of Classification Search
CPC ............. A61B 34/00–32; A61B 34/37; A61B 2034/2055; A61B 2034/2057
See application file for complete search history.

(56) References Cited

U.S. PATENT DOCUMENTS 6,671,581 B2 * 12/2003 Niemeyer ............... A61B 34/70
600/109
6,926,709 B2 * 8/2005 Bieger ............... A61B 1/00149
600/102

(Continued)

OTHER PUBLICATIONS

Xiaoli Zhang et al., Application of Visual Tracking for Robot-Assisted Laprascopic Surgery (May 16, 2005), Experimental Robotics Labratory, Simon Fraser University (Year: 2005).*

(Continued)

*Primary Examiner* — Angela M Hoffa
*Assistant Examiner* — Virag B Patel
(74) *Attorney, Agent, or Firm* — Avery N. Goldstein; Blue Filament Law PLLC

(57) ABSTRACT

Systems and processes are provided that utilize the accuracy and adaptability of an optical tracking system to track an object by maintaining a line of sight (LOS) between the optical signals from the tracked object and the optical receivers regardless of the position and orientation of the object being tracked. LOS is maintained without having to manually adjust a tracked device or the optical receivers, or be limited to a specified working volume. Instead, whenever the tracked device moves, an active controller device calculates new values for the degrees of freedom of a series of joints holding a tracking array to the tracked object to (Continued)

position and orient the tracking array to maintain visibility to the optical receivers. A computer-assisted or robotic device that decreases operating times, and improves surgical accuracy, without additional user requirements or adjustments to maintain the LOS of the optical tracking system is provided.

15 Claims, 20 Drawing Sheets

(51) Int. Cl.
    *A61B 34/32*     (2016.01)
    *A61B 34/37*     (2016.01)
    *A61B 90/00*     (2016.01)
    *A61B 90/50*     (2016.01)

(52) U.S. Cl.
    CPC ........... *A61B 2034/2048* (2016.02); *A61B 2034/2055* (2016.02); *A61B 2034/2057* (2016.02); *A61B 2034/2059* (2016.02); *A61B 2090/502* (2016.02)

(56) References Cited

U.S. PATENT DOCUMENTS

| | | | |
|---|---|---|---|
| 9,439,556 B2* | 9/2016 | Pandya | B25J 9/1682 |
| 9,717,461 B2* | 8/2017 | Yu | A61B 5/721 |
| 2002/0087101 A1* | 7/2002 | Barrick | A61B 5/1077 |
| | | | 600/587 |
| 2005/0273199 A1* | 12/2005 | Ban | B25J 9/1682 |
| | | | 700/248 |
| 2006/0142657 A1* | 6/2006 | Quaid | G06F 19/00 |
| | | | 600/424 |
| 2009/0055024 A1 | 2/2009 | Kay | |
| 2010/0299101 A1* | 11/2010 | Shimada | G09B 23/28 |
| | | | 702/150 |
| 2013/0060278 A1 | 3/2013 | Bozung et al. | |
| 2013/0331644 A1* | 12/2013 | Pandya | B25J 9/1682 |
| | | | 600/102 |
| 2013/0345718 A1* | 12/2013 | Crawford | A61B 17/025 |
| | | | 606/130 |
| 2014/0039517 A1 | 2/2014 | Bowling et al. | |
| 2014/0039520 A1 | 2/2014 | Haider et al. | |
| 2014/0188132 A1 | 7/2014 | Kang | |
| 2014/0288710 A1 | 9/2014 | Ikenaga et al. | |
| 2015/0297177 A1* | 10/2015 | Boctor | A61B 8/4218 |
| | | | 600/437 |
| 2016/0000516 A1* | 1/2016 | Cheng | A61B 34/20 |
| | | | 600/424 |
| 2017/0143429 A1* | 5/2017 | Richmond | A61B 5/064 |
| 2017/0239007 A1* | 8/2017 | Crawford | A61B 17/025 |

OTHER PUBLICATIONS

Pandya et al., A Review of Camera Viewpoint Automation in Robotic and Laprascopic Surgery (Aug. 14, 2014), Multidisciplinary Digital Publishing Insitutute, Robotics 2014 (Year: 2014).*
International Search Report dated Jul. 29, 2016 for International Application No. PCT/US2015/056940 filed Oct. 22, 2015.

* cited by examiner

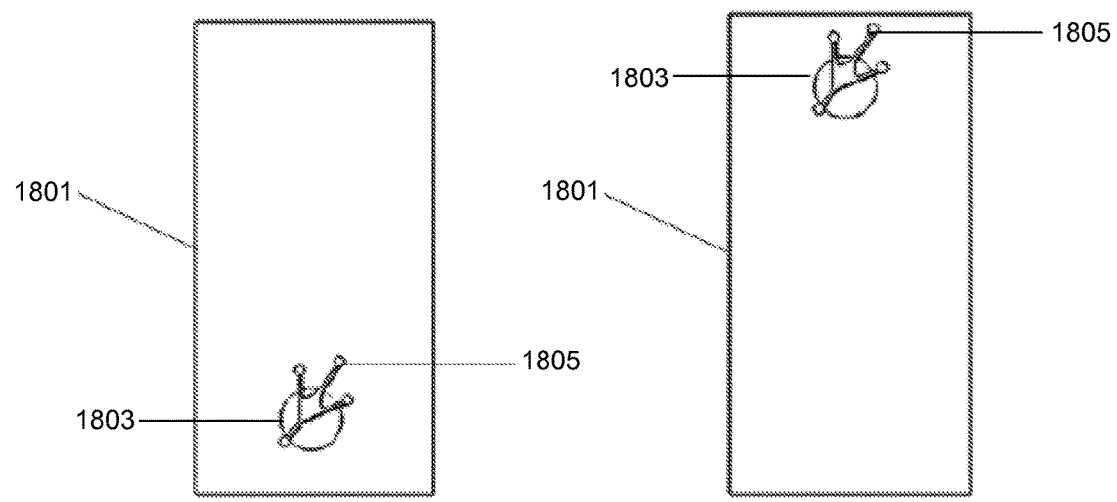
FIG. 18B
FIG. 18C

ACTIVELY CONTROLLED OPTICAL TRACKER WITH A ROBOT

CROSS-REFERENCE TO RELATED APPLICATION

This application claims priority of U.S. Provisional Patent Application Ser. No. 62/067,001 filed Oct. 22, 2014, and U.S. Provisional Patent Application Ser. No. 62/161,693 filed May 14, 2015 which are both incorporated herein by reference.

FIELD OF THE INVENTION

The present invention in general relates to the field of optical tracking; and in particular to a new and useful system to maintain a line of sight between a fiducial marker array mounted on a robot and a tracking system.

BACKGROUND OF THE INVENTION

The tracking of objects is used in many different industries ranging from military defense to computer assisted surgery. In the medical field, tracking systems have been utilized with medical devices to assist surgeons in performing precision surgery.

Typical configurations and methods for tracking objects are well known in the art. One such method exploits the emission or reflection of signals (light, radiofrequency, infrared) attached to an object, wherein the signals are detected by receivers (photodiodes, CMOS or CCD cameras). The signals are then processed to locate the position and orientation (POSE) of the object. Likewise, receivers may detect patterns, sequences, shapes, or characters attached to an object that may also be processed to determine the POSE of the object. In particular, optical tracking systems utilizing infrared or visible light are commonly used due to their accuracy and adaptability.

However, a common problem or limitation of such optical tracking systems is the need to maintain a line of sight (LOS) between the optical signals and the optical receivers. For example, when an object that is being the tracked is in motion, different orientations, positions or other objects may cause a disruption in the LOS between the optical signals and the optical receivers. Once the LOS is obstructed, the object can no longer be tracked. Other tracking systems have been developed to overcome the LOS problem. For example, electro-magnetic tracking systems (EMTS) can be used without the LOS limitation; however EMTS is not suitable in an operating room due to the potential electro-magnetic interference with other equipment and is currently less accurate than optical tracking systems. Similarly, accelerometers, and gyroscopes, known as inertial measurement units, can track objects however they intrinsically accumulate error in their position and orientation measurements over time.

Furthermore, when tracking objects in a surgical setting, there may be many instances in which the LOS becomes obstructed. For example, when operating a tracked tool, optical signals rigidly fixed thereto may be visible at one stage of the procedure but may become obstructed during a subsequent stage. This may be caused by the POSE of the tracked tool during operation. Additionally, fluids, operators, as well as other objects may also obstruct the view of the optical signals to the optical receivers. Generally, when the LOS is lost, the surgical procedure must be interrupted until the LOS is reestablished. Reestablishing the LOS currently requires manual adjustment of the optical receivers and/or optical signals. In the case of computer-assisted surgery, the manual adjustments may prolong a procedure and make it more difficult to achieve a desired surgical outcome.

During computer assisted surgery, fiducial marker arrays may be used to track rigid objects, including the operative anatomy, such as the femur. Generally, the optical tracking system has certain direction or image planes that provide the highest accuracy and/or obtain the best visibility. However, some procedures require large ranges of motion for the operative anatomy; in the case of total knee arthroplasty (TKA), the range of motion can be 120 degrees or more. During a knee replacement surgery, it is common for the surgeon to articulate the tibia and the femur throughout flexion and extension to determine how well the medial and lateral ligaments are balanced. The optical signals generally have limited fields of view, which may require the use of multi-face markers, which can require complicated registration algorithms and calibration of each face independently.

Additionally, with traditional tracking systems, the optical receivers are placed in a designated position in the operating room. The optical receivers are fixed relative to the tracked objects whereby any movement of the optical receivers during operation may require re-calibration and/or registration of the tracked objects relative to the new position of the optical receivers. Due to the fixed position of the optical receivers during the procedure, the tracked objects may move out of the tracking field of view. Therefore the LOS is lost between the tracked object and the tracking system causing an interruption in the procedure until the LOS is reestablished.

Further, the accuracy of the tracking system can depend on the field of view of the optical receivers. The field of view may be a function of the angular distance between the two optical receivers as well as the POSE of a collection of optical signals (a fiducial marker array) relative to the optical receivers. A larger convergent angle between the two optical receivers results in a smaller field of view and a more accurate system. Traditional tracking systems generally have two optical receivers that are fixed relative to one another. Therefore, the system is limited in optimizing the accuracy of the tracking system as the tracked object moves relative to the optical receivers. Similarly, if the optical signals are more aligned in the field of view of the optical receivers, the accuracy of the system is also increased. In conventional optical tracking, the fiducial marker arrays are generally fixed and remain static relative to the tracked object. Thus, the POSE of the object may change such that the optical signals are skewed away from an optimal field of view for tracking.

In the example of total knee arthroplasty (TKA), with respect to prior art FIG. 1 an operating room is illustratively shown with various components of a computer-assisted surgical system. Robots or computer assisted surgical devices 101 have an end effector 106, usually a drill or burr, for preparing the femur and tibia to receive an implant. The end effector 106 is tracked or navigated relative to the bone 112 using tracking arrays 107, 113 and an optical tracking system 108. Illustratively, the robot has various prismatic and revolute joints 102, 103 that provide control or motion in various degrees of freedom. A robot end effector flange 104 provides attachment for a tool 106 to be manipulated by the robot. Upon assembly of the tracking array 107 and end effector 106 prior to surgery, the POSE's of the coordinate systems are fixed relative to each other and stored in memory to accurately track the end effector during the surgery (see for example U.S. Patent Publication 20140039517 A1) relative to the bone anatomy 112.

A monitor 111 may be in communication with the hardware and software to provide a visual display for a user. The monitor may convey to the user various information that may include patient information, workflow instructions, real-time monitoring of the procedure, safety alarms, tracking information, as well as any other useful information and/or instructions that may be needed before, during, and/or after a procedure. Information may also be conveyed to the user via a heads up display unit or Google Glass™. A user may also interact with the robotic system 101 and/or tracking system 108 to provide input into the system(s). The monitor 111 may be a touch screen wherein a user can select and/or press different options, prompts and/or perform different actions. A remote control, joystick, mouse, keyboard, pendant and the like may also be wired or wirelessly connected to the systems to provide the interactive mechanism for the user.

A tracking system 108 with at least two optical receivers 109 may be in communication with tracking hardware 110 also shown in FIG. 1. The tracking hardware 110 may be a tracking computer, tracking controller and/or any additional storage device such as RAM, ROM, and/or other non-volatile memory. The tracking hardware may store, process and/or be programmed with various software applications, data and utilities that may include image processing, filtering, triangulation algorithms, registration algorithms, and coordinate transformation processing. The tracking hardware may be further configured to receive and/or execute input data from an external device either through a wired or wireless connection. Likewise, the tracking system 108 may be in communication with other devices in the operating workspace.

However, during TKA, multiple chamfer cuts are needed to prepare the femur and tibia. The chamfer cuts required requires the end effector 106 to be positioned and oriented in various POSE's to prepare the bone whereby the LOS of the tracking array 107 and the optical receivers 109 may become obstructed. For example, the end effector 106 and tracking array 107 may be aligned with the optical receivers 109 while preparing the anterior femoral chamfer cut, but to prepare the drill holes to receive the tibial implant, the end effector 106 and tracking array 107 are oriented 90 degrees from the chamfer cut. Therefore, the line of sight between the tracking array 107 and the optical receivers 109 is limited or lost and the user needs to manually adjust the optical receivers 109 for tracking. Similarly, considering that the operating room can be a crowded environment, other objects can interfere with the LOS for tracking.

While other types of tracking systems are contemplated that utilize other forms of energy such as electromagnetic fields and acoustic energy, these tracking systems may also be hindered by certain obstructions between the energy source and their respective receivers. For example, an electromagnetic fiducial marker emits a field of energy that needs to be received by the tracking system such that the POSE of the fiducial marker and/or fiducial marker array can be determined. Any electro-magnetic field interfering device or object that obstructs the communication to the receiver may affect the accuracy of the tracking.

Thus, there exists a need for a method and system that can utilize the accuracy and adaptability of an optical tracking system to track an object by maintaining a LOS between the optical signals and the optical receivers regardless of the position and orientation of the object being tracked. There further exists a need to reduce the possibility of other objects interfering with the LOS. There also exists a need for a method and system to provide continuous tracking of a computer-assisted or robotic device that decreases operating times, and improves surgical accuracy, without additional user requirements or adjustments to maintain the LOS of the optical tracking system.

SUMMARY OF THE INVENTION

A system for the optical tracking of an object is provided that includes: a fiducial marker array; an optical tracking system with one or more optical receivers configured for line of sight (LOS) communication with the fiducial marker array; one or more movable joints in mechanical communication with at least one of the fiducial marker array and the one or more optical receivers, the one or more movable joints provide degrees of freedom of movement to at least one of the fiducial marker array and the one or more optical receivers; and one or more controllers that actuate the one or more movable joints to maintain LOS between the fiducial marker array and the one or more optical receivers.

A process to maintain a line of sight (LOS) between a fiducial marker array and one or more optical receivers is provided that includes: positioning one or more optical receivers in an initial location that minimizes LOS disruption within a system; articulating the fiducial marker array with the one or more movable joints to an initial orientation that optimizes the fiducial marker array within a field of view of the one or more optical receivers; recording an initial position and orientation (POSE) of the fiducial marker array; calculating the changes in the POSE of the fiducial marker array; determining the difference between the calculated POSE and the initial POSE of the fiducial marker array; and articulating the one or more movable joints based on the determining to reorient the fiducial marker array to maintain the LOS.

BRIEF DESCRIPTION OF THE DRAWINGS

The present invention is further detailed with respect to the following drawings that are intended to show certain aspects of the present invention, but should not be construed as a limit on the practice of the present invention.

FIGS. 18A, 18B and 18C illustratively show an example of an optical tracking system with independently actuated optical receivers in accordance with embodiments of the invention.

DESCRIPTION OF THE INVENTION

Figure 1:
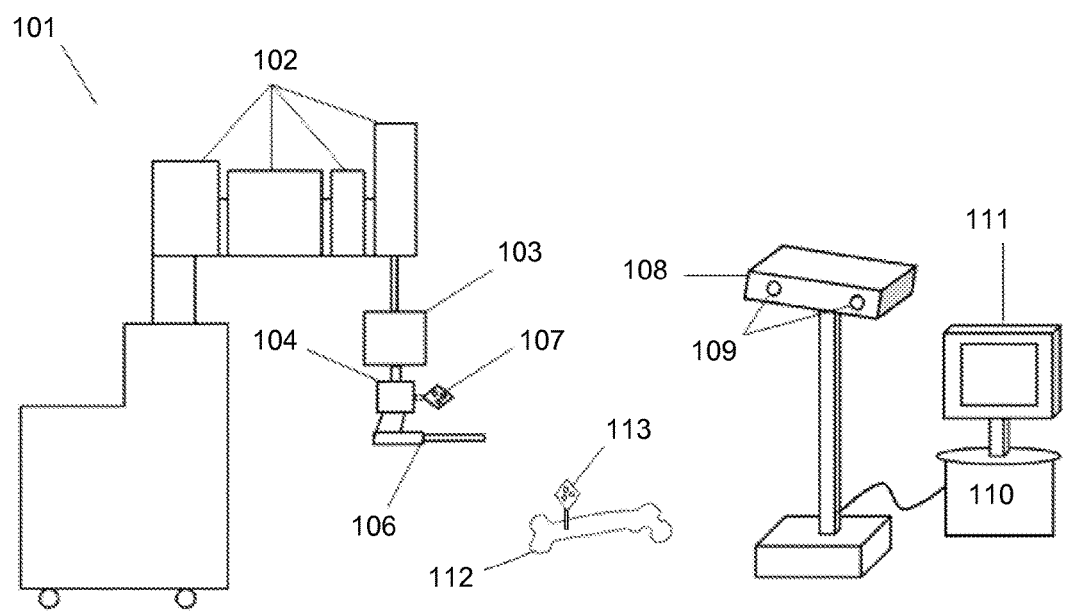
FIG. 1 illustratively depicts an operating room with a prior art computer-assisted device with a fixed fiducial marker array and an optical tracking system to track the position and orientation of a tool.

The invention disclosed herein describes a system and process for the optical tracking of an object, and more particularly to an active controller device incorporated on a computer-assisted device that maintains the line of sight between a tracking array and an optical receiver.

It is to be understood that in instances where a range of values are provided, the range is intended to encompass not only the end point values of the range but also intermediate values of the range as explicitly being included within the range and varying by the last significant figure of the value. By way of example, a recited range from 1 to 4 is intended to include 1-2, 1-3, 2-4, 3-4, and 1-4.

As used herein, the term 'tool' may be any instrument capable of performing work on an external object. Tools illustratively include a probe, drill bit, laser, cutter, burr, saw blade, shears, forceps, dissectors, cautery hook, cautery spatula, scissors, retractors, graspers; as well as any assembly used to house and/or operate the object contacting instrument.

The term, 'communication' is used to refer to the sending and/or receiving of data, and/or energy either through a wireless or electrical connection unless otherwise specified. Such 'communication' may be accomplished by means well known in the art such as Ethernet cables, BUS cables, Wi-Fi, Bluetooth™, and the like. The 'communication' and/or wireless sending and/or receiving of data and/or energy, referenced throughout the description, may also be accomplished using visible light as described in U.S. Provisional Patent Application Nos. 62/083,052 and 62/111,016 which are both hereby incorporated by reference in their entirety.

As used herein, a marker or a fiducial marker refers to an object that provides a point of reference. Examples of a marker or a fiducial marker may include an active transmitter, such as a light emitting diode (LED) or electromagnetic emitter, a passive reflector, such as a plastic sphere with a retro-reflective film, a distinct pattern or sequence of shapes, lines and/or other characters, acoustic emitters and/or reflectors, and the like. A tracking array or fiducial marker array is referred to as an arrangement of two or more markers or fiducial markers in/on a rigid body of any geometric shape. The end effector flange referred to herein is the attachment point between the robot and the end effector (tool or instrument).

The present invention has utility to track an object using an optical tracking system. In particular inventive embodiments, the tracking is continuous. Optical tracking systems rely on line of sight (LOS) for tracking whereby the present invention provides a system and process to maintain the LOS on a robot or computer-assisted device. By using the invention disclosed herein, the user will not have to manually adjust the device or the optical receivers, or be limited to a specified working volume to maintain the LOS for tracking. Instead, whenever the robot moves, an active controller device calculates new values for the degrees of freedom of the joints to position and orient the tracking array to maintain visibility to the optical receivers.

The following description of various embodiments of the invention is not intended to limit the invention to these specific embodiments, but rather to enable any person skilled in the art to make and use this invention through exemplary aspects thereof.

Disclosed herein is the use of a tracking system. General tracking systems may include at least one receiver to detect at least one fiducial marker. The receiver(s) are coupled to at least one processor for processing the receiver output. The processing may then determine the position and/or orientation of the fiducial marker and/or fiducial marker array. The receiver may detect the fiducial marker through a variety of mechanisms illustratively including, but not limited to, optical energy, electromagnetic energy, infrared energy, ultraviolet energy, magnetic energy, acoustic energy, targeted visible light, as well as shape, pattern, line, sequence or character recognition. As a general tracking system has been described here, other specific inventive embodiments of a tracking system may be further detailed in the description below. Additionally, for clarity and conciseness, an optical tracking system that utilizes electromagnetic radiation is provided as an illustrative example; however, it should be appreciated that other tracking systems may also be utilized by the subject matter disclosed herein.

Also referenced herein are computer-assisted surgical systems which are to be considered synonymous with computer-aided surgical system, robotic surgical systems, navigation assisted surgical system, image-guided surgical systems and the like. Such systems illustratively include for example the NavioPFS™ Robotic Resurfacing System (Blue Belt Technologies), the RIO® Robotic System (Mako Surgical Corp.), the ROBODOC™ Surgical System (Think Surgical), or any other computer-controlled device. It should also be appreciated that other non-computer controlled instruments, tools as well as any other object that may require tracking may be utilized by the subject matter disclosed herein. Additionally, as total knee arthroplasty is provided as an illustrative application, it should be appreciated that other medical and non-medical applications can similarly exploit the subject matter disclosed herein.

Embodiments of the present invention generally describe a system consisting of at least one fiducial marker array, an optical tracking system with optical receivers, and a movable joint in mechanical communication with at least one of the fiducial marker array or optical receivers to adjust the fiducial marker array or optical receivers such that the LOS is maintained or the field of view of the tracking system is optimized. Multiple systems and methods for accomplishing such a task is further detailed in the various embodiments described below.

Active Fiducial Marker Array with a Robot

Figure 2:
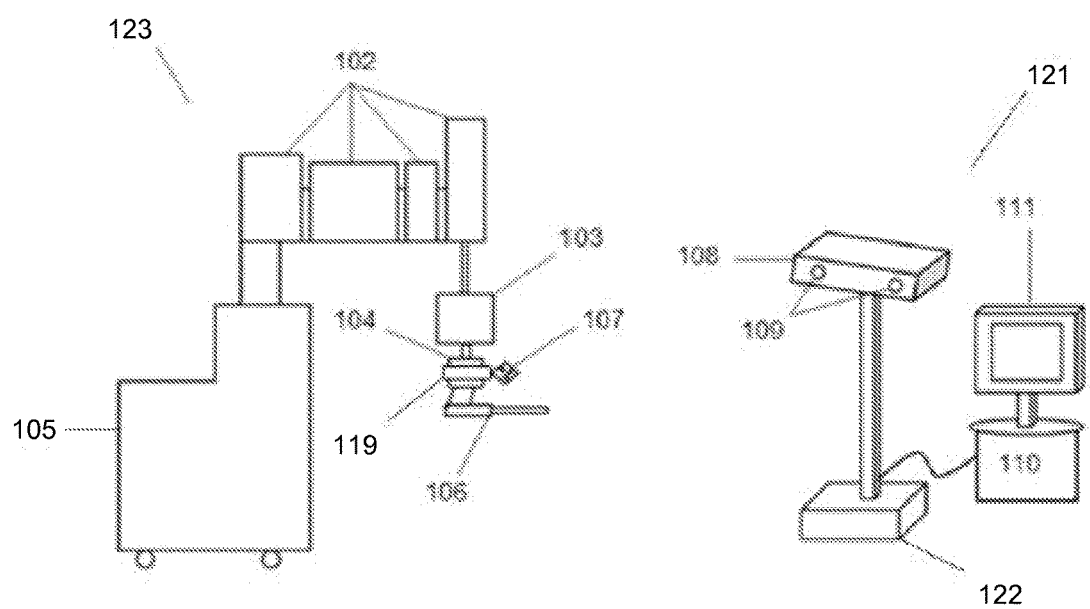
FIG. 2 illustratively depicts an operating room with a computer-assisted device with a fiducial marker array and an optical tracking system to track the position and orientation of a tool in accordance with embodiments of the invention.

In a specific inventive embodiment, with reference to FIG. 2, an operating room is illustratively shown with various components of a computer-assisted surgical system. A robotic surgical system 123 (referred herein after as 'robot') may have a base 105 and various joints and links 102, 103 to provide one or more degrees of freedom to articulate a tool 106 attached to an end effector flange 104. The POSE of each of the joints 102, 103 may be detected and articulated by encoders and motors, respectively. The motors and encoders may be calibrated with robotic hardware and software such that the POSE of the tool 106 may be precisely known in space. The robotic hardware may include one or more robotic computer(s) (not shown), robotic controller(s) (not shown) and/or any additional storage devices such as RAM, ROM or other non-volatile memory. The robotic hardware may be located within the robot base 105 or housed externally. The robotic hardware may store, process, execute and/or be programmed with various software applications, data and utilities that may include robotic control, computer-aided machining (CAM) instructions, kinematic processing, calibration routines, bounded virtual environments, implant data, real-time robot monitoring (e.g., position, velocity, acceleration information), real-time safety monitoring, registration algorithms, medical imaging data, procedural workflow instructions as well as any other software, data or utilities that may be required to operate the robot 123, execute a procedure, or guide a user throughout a procedure. The robotic hardware may be further configured to receive and execute input data from an external device either through a wired or wireless connection. The input data may be patient information, medical imaging data, implant data, CAM instructions, software upgrades, tracking information from the tracking system or optical receivers, as well as any additional software applications to be executed by the robotic hardware. Likewise, the robot 123 may be in communication with other devices in the operating workspace.

A tracking system 121 with at least one optical receiver 109 may be in communication with tracking hardware 110 also shown in FIG. 2. The tracking hardware 110 may include a tracking computer, tracking controller and/or any additional storage device such as RAM, ROM, or other non-volatile memory. The tracking hardware 110 may store, process, and/or be programmed with various software applications, data and utilities that may include image processing, filtering, triangulation algorithms, registration algorithms, and coordinate transformation processing. The tracking hardware 110 may be further configured to receive and/or execute input data from an external device either through a wired or wireless connection. Likewise, the tracking system 121 may be in communication with other devices in the operating workspace.

Additionally, it should be appreciated that although robotic hardware/software and tracking hardware/software have been described as separate components, it is quite possible that various configurations of the hardware and software may be inventively assembled to successfully track an object, control a robot and perform a medical procedure. For example, the different software, data and utilities may be stored, processed and/or executed on one or more hardware component(s) that may be connected and/or communicate by a variety of different methods. The hardware component(s) may also be located in one or more locations that may illustratively include the robot base 105, an optical receiver housing 108, a surgical light, the base of an optical receiver supporting structure 122, housed externally and any combination thereof. Therefore, the robotic hardware/software and tracking hardware/software will be referred to collectively as hardware and software henceforth unless otherwise specified.

A monitor 111 may be in communication with the hardware and software to provide a visual display for a user. The monitor may convey to the user various information that may include for example, patient information, workflow instructions, real-time monitoring of the procedure, safety alarms, tracking information, as well as any other useful information or instructions that may be needed before, during, or after a procedure. Information may also be conveyed to the user via a heads up display unit or Google Glass™. A user may also interact with the robotic system 123 or tracking system 121 to provide input into the system(s). The monitor 111 may be a touch screen wherein a user can select or press different options, prompts and/or perform different actions. A remote control, joystick, mouse, keyboard, pendant and the like may also be wired or wirelessly connected to the systems to provide the interactive mechanism for the user.

In one embodiment of the invention, prior to tracking an object or end effector, optical receivers 109 are positioned in a location that will least likely cause a LOS disruption within the space of tracking. For example, in an operating room, the optical receivers 109 can be positioned on the ceiling, or a particular wall whereby other objects and operators are least likely to interfere with the line of sight of the robot 123 and the optical receivers 109.

Figure 3:
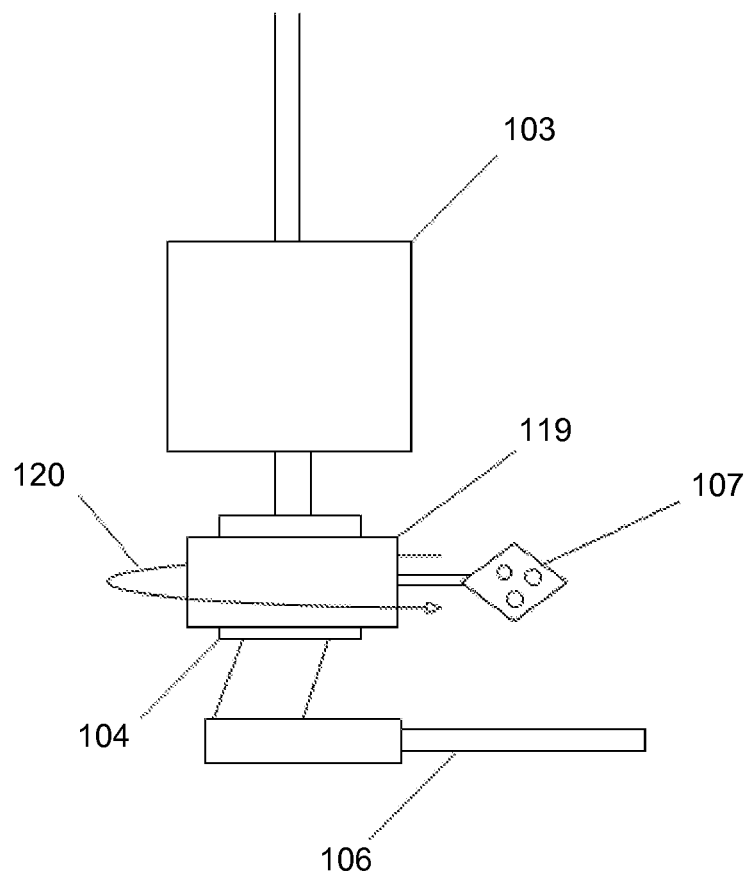
FIG. 3 is a schematic of an embodiment of the inventive system with an active device incorporated on the end effector flange to maintain optical tracking line of sight.

A zoomed in view of the end effector of the robot 123 is illustratively shown in FIG. 3. A fiducial marker array 107 may be attached to and/or fixed in a position and orientation to a movable joint 119. The movable joint 119 may be in direct communication with the hardware and software of the robot 123. The movable joint 119 may also include an additional active movable joint controller (not shown) that is in communication with the hardware and software. In one inventive embodiment the additional active controller of the movable joint 119 may be located in the robot 123, or the end effector flange 104. In another inventive embodiment, the active controller is incorporated within the movable joint 119 electrically or wirelessly connected to the robot. The movable joint 119 may further include at least one position and/or rotation sensor(s), such as encoders for measuring the local coordinates of the movable joint 119 to establish a position or orientation of the movable joint 119. In another inventive embodiment, the movable joint 119, active controller and one or more encoders and any combination thereof are incorporated with the end effector flange 104 and in communication with the robot 123. The active controller is further adapted to receive position and orientation data from the hardware and software, the movable joint position or rotation sensor(s), as well as any other position or orientation data collected from the various mechanisms described herein.

The movable joint 119 may be attached to and/or incorporated with the end effector flange 104 of the robot 123; however it should be appreciated that the movable joint 119 may be attached and/or incorporated on any of the robot joints and links (102, 103) or the robot base 105. The movable joint 119 may provide at least one degree of freedom (illustratively shown as arrow 120) to articulate the fiducial marker array 107 independent of how the tool 106 is articulated by the various links and joints (102, 103) of the robot 123. The movable joint 119 may articulate the fiducial marker array 107 such that the LOS is maintained or the field of view is optimized. One or more tracking arrays 113 are attached to a patient's anatomy 112 and registered with a 3-D model of the bone to fix the POSE of the coordinate system of the bone 112 with the tracking array 113 and with respect to the coordinate frame of the optical receivers 109.

This may be accomplished by several different methods.

Figure 4:
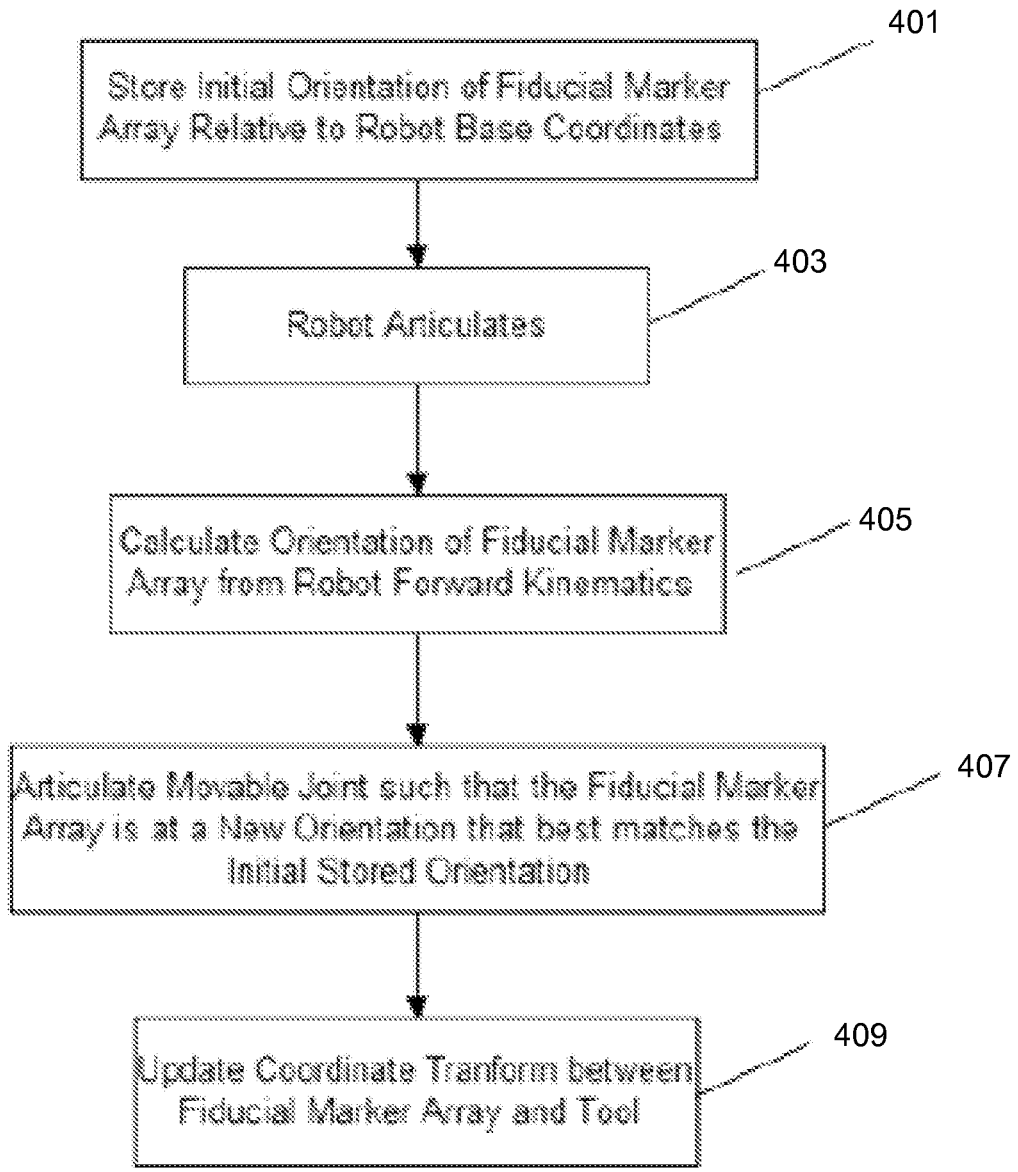
FIG. 4 is an illustrative flow chart of a method for actively articulating a fiducial marker array in accordance with embodiments of the invention.

For example in conjunction with the flowchart of FIG. 4, in a particular inventive embodiment, prior to tracking the tool 106, the optical receivers 109 are positioned in a location that will least likely cause a LOS disruption within the space of tracking. This location may illustratively be for example, on the ceiling, attached to or incorporated in a surgical light, placed on a particular wall, or connected to a supporting structure 122. The movable joint 119 may then be manually or automatically articulated such that the fiducial marker array 107 is initially oriented in an optimal location within the field of view of the optical receivers 109. The initial optimal location may be determined visually by the user, by the hardware/software, or a combination thereof. For example, the hardware/software may determine that the fiducial marker array 107 is in the optimal POSE when the tracking error is minimal. Or, if the fiducial marker array 107 is manually moved, the hardware/software may relay a signal or cue to the user via a monitor 111 when the POSE of the fiducial marker array 107 is optimal.

Subsequently, the coordinate frames/systems of the tool 106, fiducial marker array 107, movable joint 119, robot 123, and optical receiver/tracking system 121 may be calibrated relative to one another at this position and orientation using techniques well known in the art. Therefore, the relative POSE and transformations between the tool 106, the fiducial marker array 107 and the movable joint 119 are all known relative to one another and with respect to the robot coordinates and/or tracking system coordinates. The POSE of the fiducial marker array 107 at the initial optimal location may then be recorded and stored within the hardware/software with respect to the robot base coordinates (Block 401) and used as the future optimal LOS reference orientation. Then, as the tool 106 and various joint/links (102, 103) (Block 403) of the robot 123 articulate, either autonomously and/or moved manually by a user, the POSE of the fiducial marker array 107 may be calculated from the forward kinematics of the robot (Block 405). The forward kinematics may be determined by the encoder values incorporated with each robot joint 102, 103. It should be noted that one of ordinary skill in the art will recognize that depending on where the movable joint 119 is located on the robot (e.g., on the base robot 105, between two joints 102 and 103 of the robot, or on the end effector flange 104) will determine how the forward kinematics is computed and where the fiducial marker array 107 is located. The hardware/software or active movable joint controller may then calculate the difference between:

1. the current location of the fiducial marker array 107 from the forward kinematics (Block 405), and
2. the initially stored orientation (Block 407).

The calculated difference may provide the corresponding degree to which the movable joint 119 must be articulated such that the fiducial marker array 107 is re-oriented in a position that may best match the initially stored orientation (Block 407). The joint command may be sent from the hardware/software or active movable joint controller. As a simple example, if the tool 106 and fiducial marker array 107 are rotated 180 degrees by a robot joint (102, 103), the fiducial marker array 107 may no longer be in the LOS of the tracking system. From the forward kinematics, the hardware/software knows that the fiducial marker array is now oriented 180 degrees away from the tracking system. The hardware/software or the active movable joint controller may send a joint command to the movable joint 119 to rotate the fiducial marker array 107 another 180 degrees, independent of the other joints (102, 103) of the robot 123, such that the fiducial marker array 107 is now in the LOS of the optical receivers 109.

Thus, the kinematics define the position and location of the end effector 106 during robotic movement and is used with the active controller controlling the movable joint 119 to re-locate the tracking array 107 by at least one degree of freedom 120 in a new position and/or orientation that best aligns with the position and orientation of the optical receivers 109 that was designated prior to tracking. Therefore, the tracking array is re-positioned in a location that will least likely cause a disruption in the LOS with the optical receivers 109 while the end effector 106 is moving or has moved to a new location. Furthermore, the accuracy of the tracking is not compromised during robotic movement and the likelihood of maintaining a continuous LOS between the tracking array 107 and the optical receivers 109 is accomplished.

Figure 5:
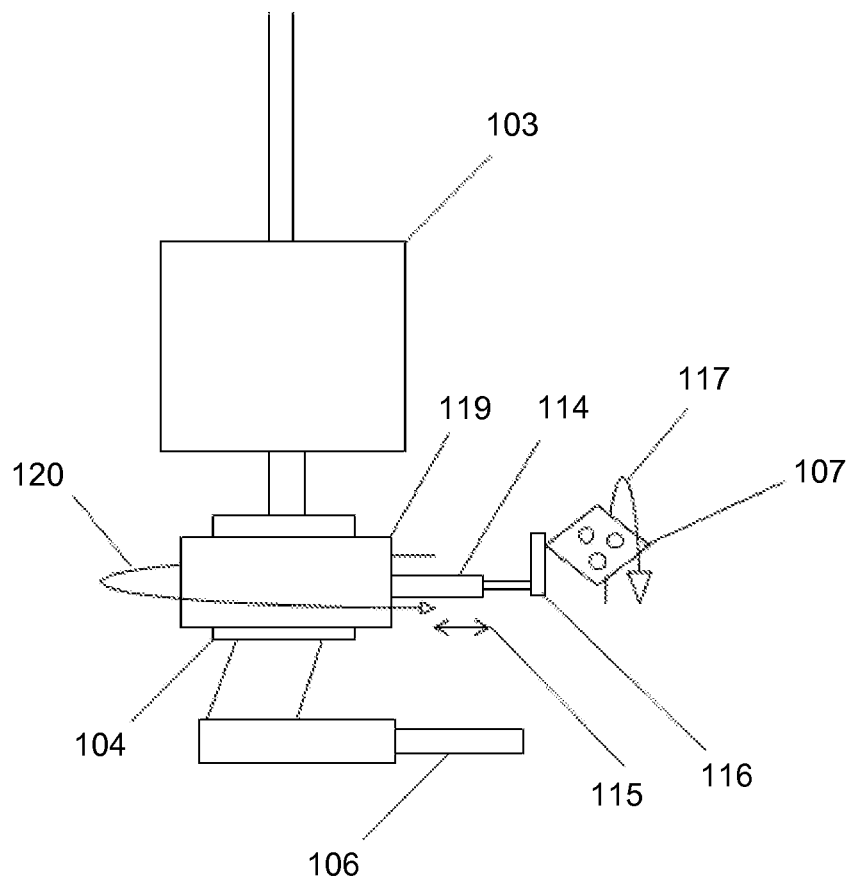
FIG. 5 illustratively depicts a multiple degree of freedom active fiducial marker array in accordance with embodiments of the invention.

In the case of a movable joint 119 with only one degree of freedom as illustratively shown in FIG. 3, it may be impossible to position and/or orient the fiducial marker array 107 at the same initially stored orientation due to the POSE of the other joints (102, 103) of the robot 123 and the allowable degree of freedom provided by the movable joint 119. Thus, in a particular inventive embodiment, multiple movable joints may be assembled or incorporated with the robot 123 and the fiducial marker array 107 to provide additional degrees of freedom. The additional joints are used to attach the tracking array 107 to the movable joint 119. As an illustrative example, with reference to FIG. 5, a prismatic joint 114 may provide linear motion (arrow 115), while an additional revolute joint 116, may add another degree of freedom (arrow 117). Depending on the number of degrees of freedom provided by the movable joints (119, 114,116), the hardware/software or active movable joint controller may additionally or optionally compute the new position and/or orientation by minimizing the difference between:

1. the calculated orientation of the fiducial marker array 107 from the robot kinematics, and
2. the initially stored orientation.

The hardware/software or active movable joint controller may then send the joint command(s) to the movable joint(s)

(119, 114, and/or 116), such that the fiducial marker array 107 best matches the POSE of the initially stored POSE. Once the fiducial marker array 107 is re-oriented (Block 407), the coordinate transform between the tool 106 and the fiducial marker array 107 may then be updated using the encoder values from the robot joints (102, 103) and the moveable joint 119 (Block 409). Therefore, the fiducial marker array 107 may remain in the LOS of the optical receivers 109 and the POSE of the tool 106 may be accurately updated and known with respect to the tracking system coordinates. Thus a surgical procedure may be uninterrupted even if the tool 106 must be oriented in a position that would otherwise cause the LOS to be lost. It should be appreciated that although only three movable joints are illustratively shown in FIG. 5, additional movable joints may be incorporated for additional or redundant degrees of freedom to articulate the fiducial marker array 107.

In a particular inventive embodiment, the new orientation (Block 407) of the fiducial marker array 107 may then replace the initially stored orientation (Block 401) as the new reference orientation. This may be beneficial if the robot is oriented in one POSE for the first part of a medical procedure, and then completely re-oriented in a new POSE for the remainder of the medical procedure. However, it should be appreciated that the initially stored orientation (Block 401) may always be used as the orientation reference.

However, there may be some drawbacks to having a continuously articulating fiducial marker array 107. For example, errors may inherently accumulate in the transformation and kinematic calculations. There may also be latency in the various computational steps that may further hinder the accuracy and tracking speed of the tracking system 121. Additionally, during certain stages of a procedure it may be beneficial for the fiducial marker array 107 to remain fixed relative to the tracked object such that the speed and accuracy of the tracking system are optimal.

Figure 6:
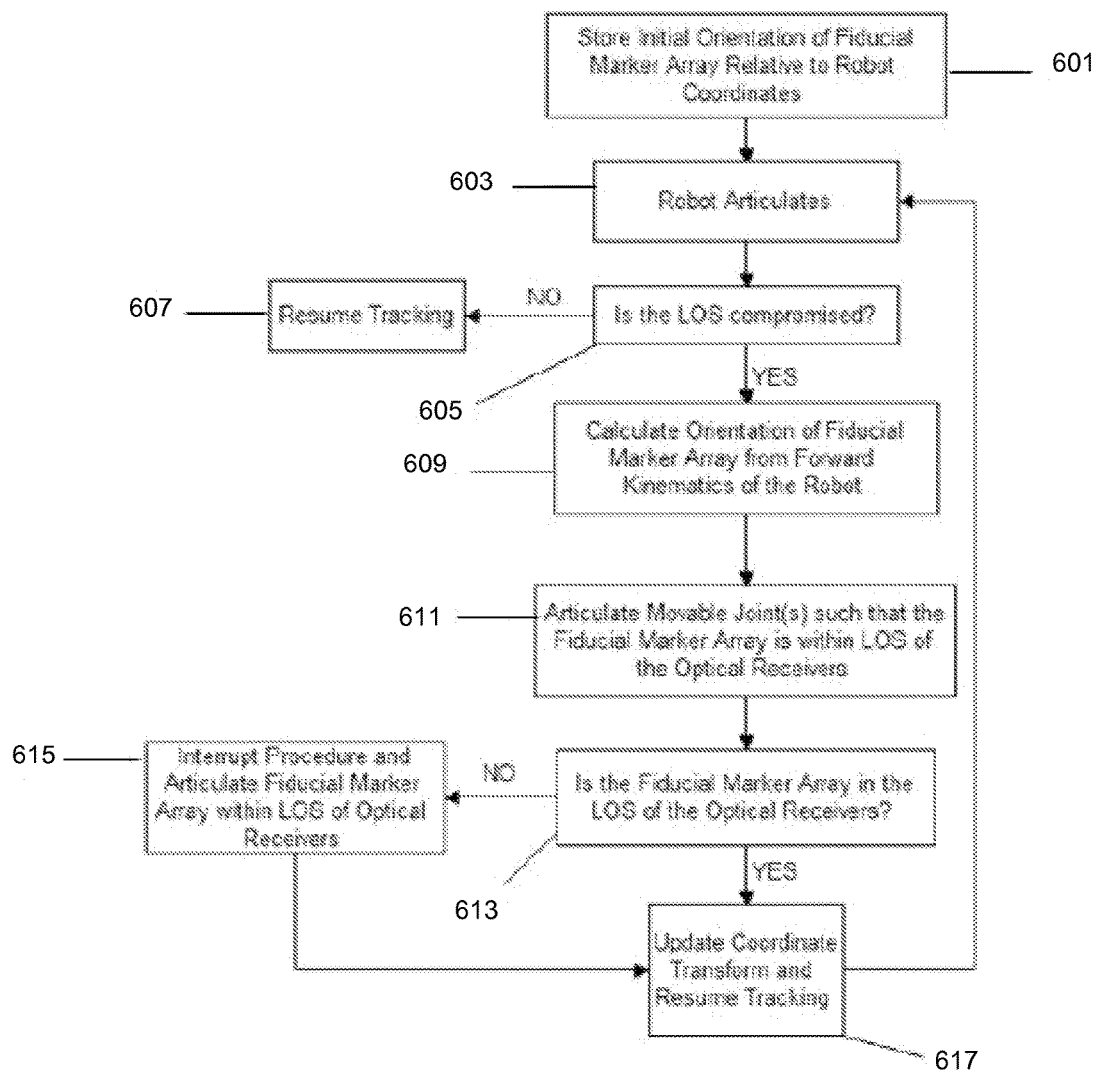
FIG. 6 is an illustrative flow chart of a method for actively articulating and monitoring a fiducial marker array relative to robot coordinates in accordance with embodiments of the invention.

Therefore, in specific inventive embodiments, other or additional methods may be employed. With reference to the flowchart of FIG. 6, the initial orientation of the fiducial marker array 107 may be stored with respect to the robot coordinates (Block 601) using the methods previously described. Subsequently, as the tool 106 and robot joints/links (102, 103) of the robot 123 articulate, either automatically or moved manually by a user (Block 603), the hardware/software may periodically monitor the LOS of the fiducial marker array 107 to determine if the LOS may be compromised (Block 605). The monitoring may be done continuously or at set time intervals that may depend on the stage of a procedure. A compromised event or error may illustratively be a function of the field of view of optical receivers 109 relative to the fiducial marker array 107, the general visibility of the optical receivers 109 relative to the fiducial marker array 107, or the accuracy of the tracking due to the POSE of the fiducial marker array 107 relative to the optical receivers 109. For example, the LOS may be compromised if the angle of the fiducial markers on the fiducial marker array 107 becomes increasingly parallel to the angle of the optical receivers 109. The LOS may be compromised if the fiducial marker array 107 is approaching the boundary of the field of view of the tracking space. Additionally, one or more fiducial markers on the fiducial marker array 107 may be partially or fully occluded resulting in a weak or lost signal. The hardware/software may monitor the LOS and be programmed to determine if a LOS compromised event or error occurs. For example, if the hardware/software determines that the angle of the fiducial marker array 107 is at a specified threshold angle relative to the optical receivers, then the hardware/software may trigger a command that the LOS may be compromised (i.e., signaling that the angle between the fiducial marker array 107 and optical receivers 109 are too parallel). If no such command, threshold, or any other trigger signaling that the LOS may be compromised, the tracking resumes (Block 607). If the LOS may be or has become compromised then the orientation of the fiducial marker array 107 may be updated.

The fiducial marker array 107 may be updated using techniques as previously described. For example, the hardware/software may calculate the orientation of the fiducial marker array 107 from the robot forward kinematics (Block 609). The hardware/software or active movable joint controller may then calculate and send joint command(s) to the movable joint(s) (119, 114 and/or 116) to articulate the fiducial marker array 107 such that the new orientation best matches the initially stored orientation (Block 611) as previously described. An additional check may then be performed wherein the hardware/software detects if the LOS has been restored or the compromised event has been alleviated (Block 613). If the LOS has not been restored or an error still exists, then the procedure may be interrupted. In a particular inventive embodiment, the movable joint may then articulate the fiducial marker array 107 automatically in different POSE as allowed by the degree(s) of freedom of the movable joint(s) 119. The hardware/software may then locate a POSE wherein the fiducial marker array 107 is within the LOS of the optical receivers 109 and no compromised errors exist (Block 615). At which point, the coordinate transforms may be updated from the encoder values incorporated with the joints and the procedure may resume (Block 617).

Figure 7:
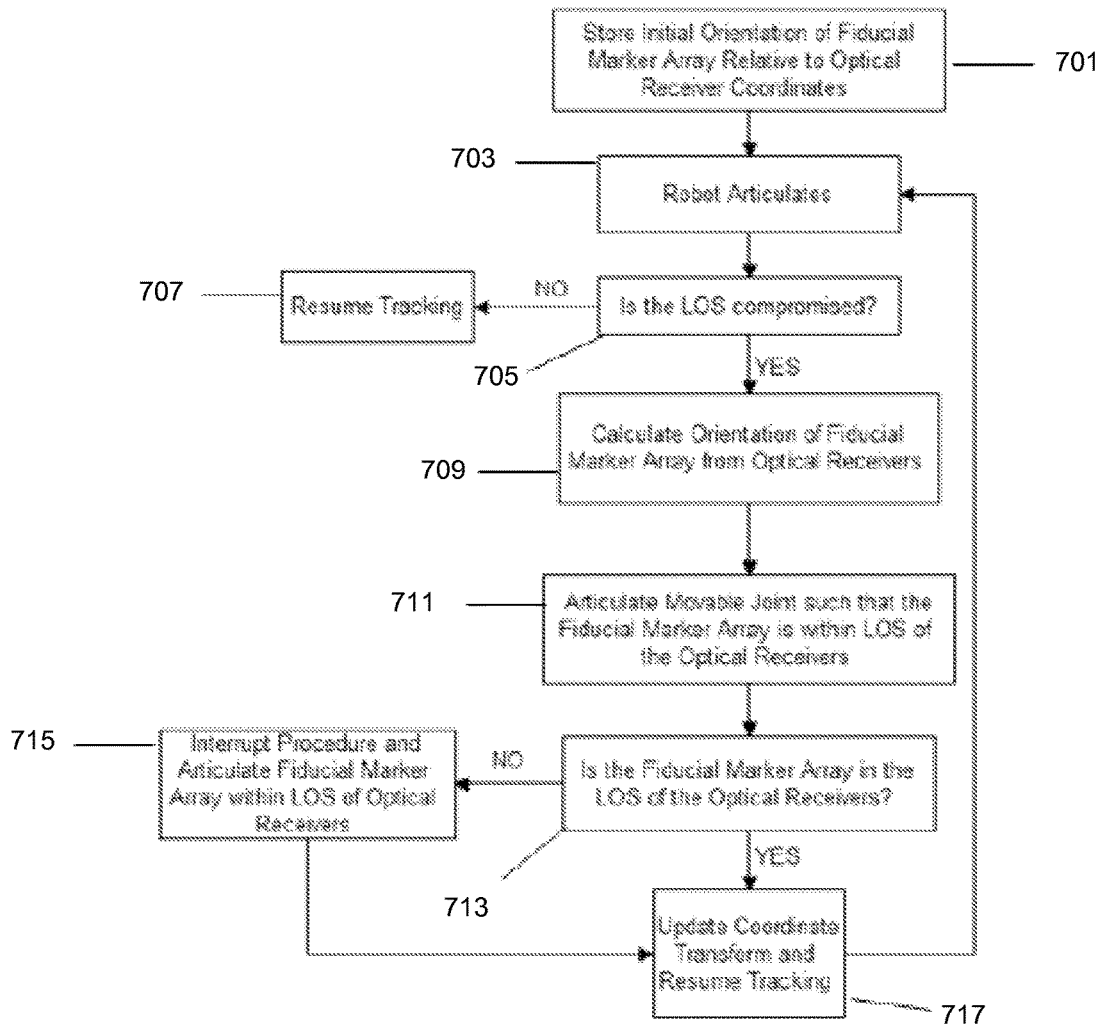
FIG. 7 is an illustrative flow chart of a method for actively articulating and monitoring a fiducial marker array relative to optical receiver coordinates in accordance with embodiments of the invention.

With respect to the flowchart of FIG. 7, the fiducial marker array 107 may be re-oriented to the initially stored orientation by using the measurements from the hardware/software that processes and receives data from the optical receivers. The hardware/software may record and store an initial optimal orientation of the fiducial marker array 107 with respect to the tracking system coordinates (Block 701). As the tool 106 and joint/links 102, 103 of the robot 123 articulate, either autonomously or moved manually by a user (Block 703), the hardware/software may monitor the LOS of the fiducial marker array to determine if the LOS may be compromised (Block 705) as previously described. If the LOS is not becoming compromised then the tracking resumes (Block 707). If the LOS may become compromised, the orientation of the fiducial marker array 107 may be measured by the hardware/software that processes and receives data from the optical receivers 109 (Block 709). However, this assumes that the LOS has not been compromised to the point where the orientation of the fiducial marker array cannot be measured. The hardware/software or active movable joint controller may then calculate the difference and/or minimize the difference between:

1. the current measured POSE of the fiducial marker array 107 from the hardware/software processing the data from the optical receivers, and
2. the initially stored POSE.

The hardware/software and/or active movable joint controller may then send the corresponding joint command(s) to re-orient the fiducial marker array 107 to best match the initially stored orientation (Block 711). The additional check (Block 713), procedure interruption (Block 715), and coordinate transformation update (Block 717) may then all and/or optionally be implemented as previously described.

Figure 8:
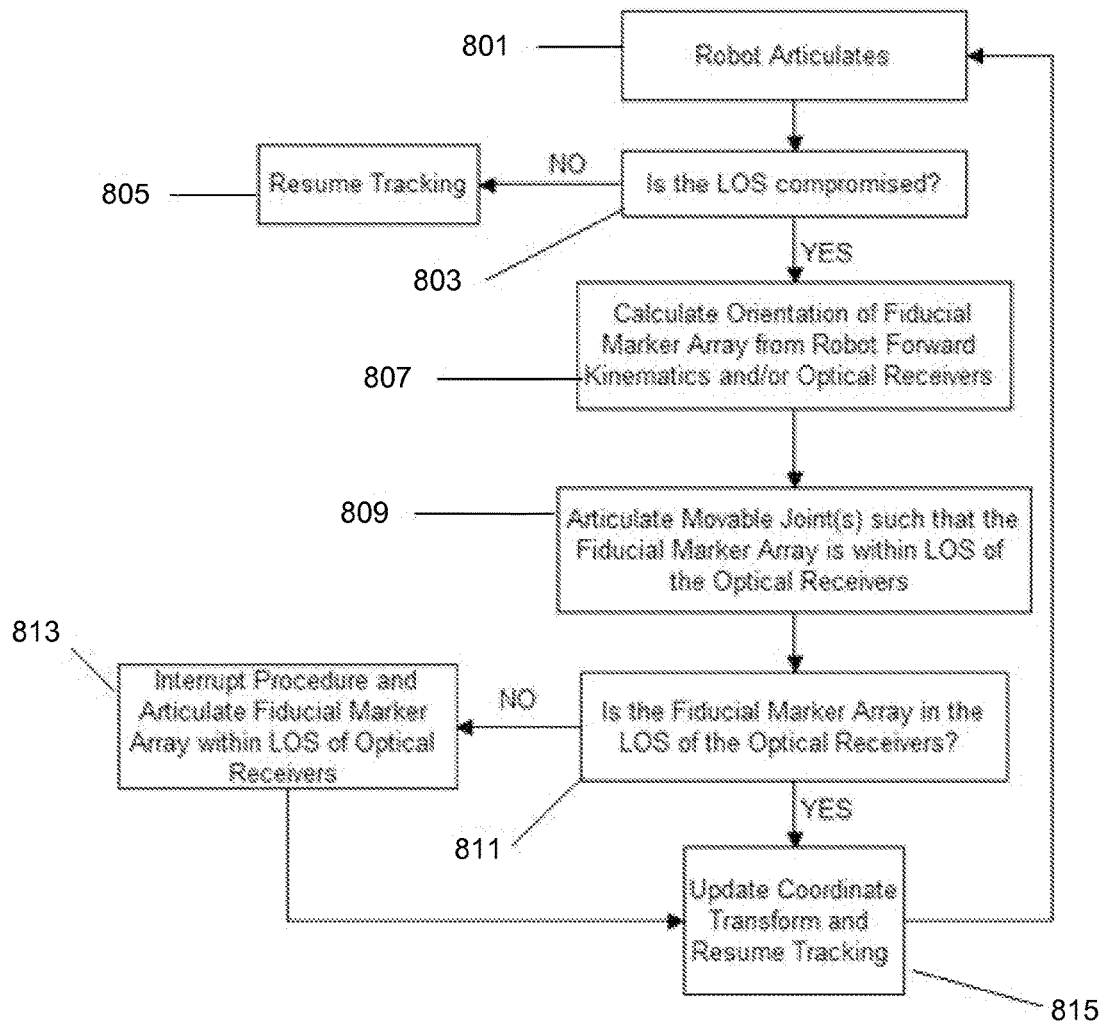
FIG. 8 is an illustrative flow chart of a method for actively articulating and monitoring a fiducial marker array relative to robot coordinates without an initially stored reference orientation in accordance with embodiments of the invention.

The step of using an initially stored position and/or orientation of the fiducial marker array 107 as a reference POSE is but one method to re-establish or optimize the LOS and field of view with the optical receivers 109. However, in particular inventive embodiments, the LOS may be re-established or optimized without an initially stored POSE. With reference to the flowchart of FIG. 8, the fiducial marker array 107 may be oriented in the field of view and LOS of the optical receivers. Subsequently, as the tool 106 and joints/links 102, 103 of the robot 123 articulate, either autonomously or moved manually by a user (Block 801), the hardware/software may monitor if the LOS may be or become compromised (Block 803). For example, if the hardware/software determines the fiducial marker array 107 is approaching a boundary of the tracking field of view, then a compromised event or error may be triggered. Similarly, the compromised event may occur due to a poor orientation of the fiducial marker array 107 relative to the optical receivers 109. If no such event is triggered then the tracking resumes (Block 805). If, however, a compromised event is triggered, then the current POSE of the fiducial marker array may be calculated either from the forward kinematics of the robot 123 and/or measured by the hardware/software processing and receiving data from the optical receivers 109 (Block 807). Since the coordinate boundaries of the tracking field of view is known by the hardware/software, the hardware/software may send a joint command to the movable joint(s) (119, 114 and/or 116) to articulate the fiducial marker array 107 such that the LOS is re-established or optimized (Block 809). The additional verification step (Block 811), procedure interruption (Block 813) and coordinate transform update (Block 815) may then all or optionally be implemented as previously described.

In a particular inventive embodiment, the LOS may be optimal when the fiducial marker array 107 is directly perpendicular in the LOS of the optical receivers 109, wherein a compromised event occurs when the perpendicularity is outside a specified threshold. For example, a vector normal to the fiducial marker array plane may be calculated from the measured POSE of three fiducial markers residing on the fiducial marker array 107. If the normal vector is pointed directly toward the imaging plane of the optical receivers 109, then the fiducial marker array 107 is perpendicular to the optical receivers 109. A LOS compromised event may then occur if the calculated normal vector drifts away, within a specified threshold, from the optical receivers 109. It is also contemplated that an initially stored normal vector may also be stored with the stored initial orientation (e.g. Block 601 of FIG. 6) information and used to reestablish the LOS, or optimize the LOS or field of view subsequently.

Fiducial Marker Array with Robot Joints/Links

In specific inventive embodiments, the fiducial marker array 107 may be attached and/or incorporated with one of the joints (102, 103) of a robot 123 with 6 degrees or more of freedom. The fiducial marker array 107 may be positioned and/or oriented to maintain the LOS with the optical receivers 109 by using a redundant axis of a 7 degree of freedom robot, or by using a specific configuration of a 6 degree of freedom robot. This is due to the fact that multiple joint solutions may exist, whereby a tool 106 may still reach and perform a task on a target area. A robot with 6 degrees or more of freedom may position a tool 106 in a specific location using different positions and/or orientations of the various links (102, 103) that make up the robot 123. In certain circumstances, depending on the final target position of the tool 106, the joint (102, 103) with the fiducial marker array 107 may re-adjust to maintain the LOS with the optical receivers 109 without changing the tool 106 position. In the case of a robot with 7 degrees of freedom or more, the fiducial marker array may be attached to the joint that provides the redundant degree of freedom. Therefore, the redundant axis may be controlled to adjust the fiducial marker array 107 in the LOS of the optical receivers 109.

Figure 9:
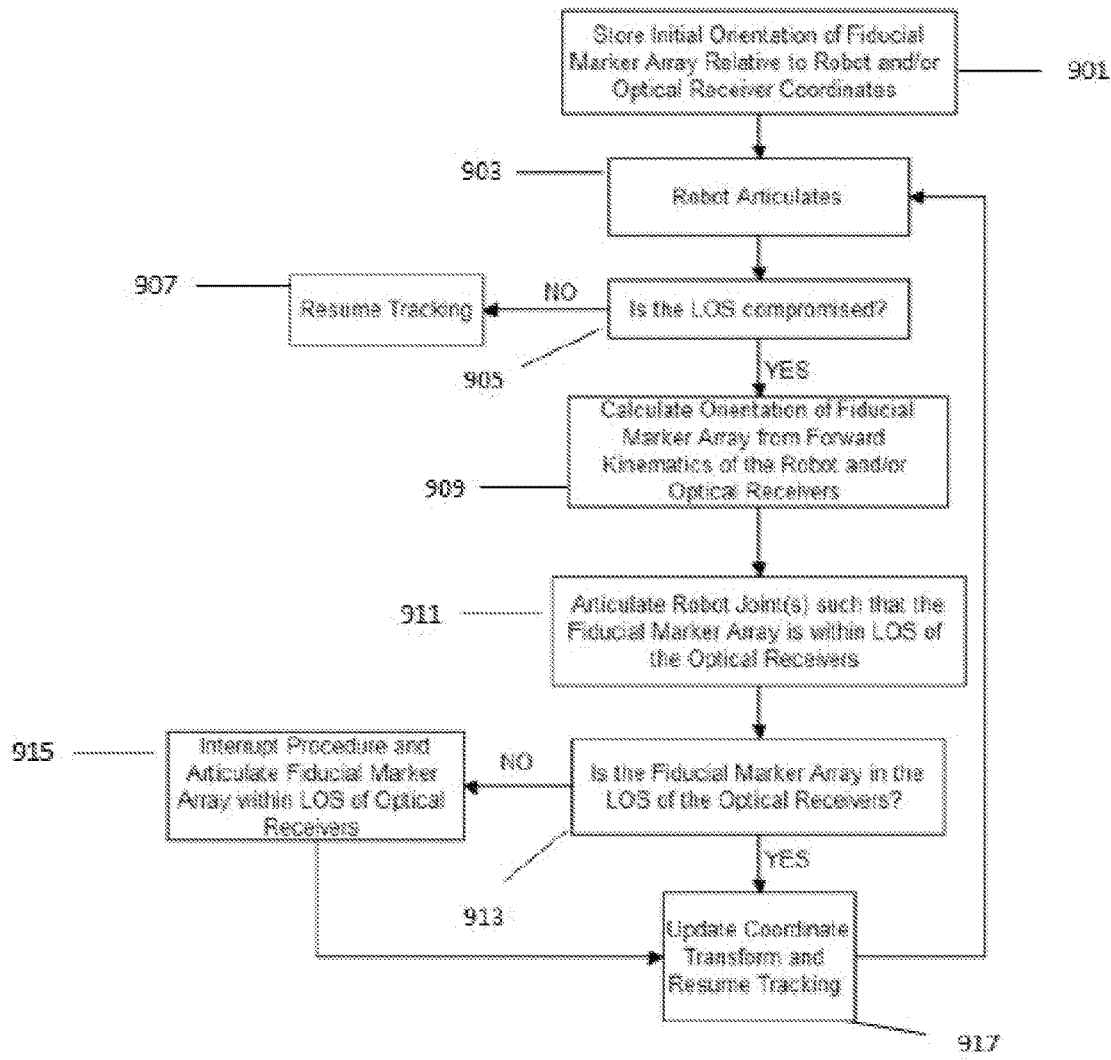
FIG. 9 is an illustrative flow chart of a method for actively articulating and monitoring a fiducial marker array attached to a robots joints/links in accordance with embodiments of the invention.

In an illustrative example, with reference to the flowchart of FIG. 9, the initial POSE of the fiducial marker array 107 may be stored by the hardware/software or active movable joint controller, in robot and/or tracking system coordinates (Block 901). Subsequently, as the tool 106 and joint/links 102, 103 of the robot 123 articulate, either autonomously or moved manually by a user (Block 903). During articulation, the hardware/software may determine if the LOS may become or is compromised as previously described (Block 905). If there is no compromised then the tracking may resume (Block 907). If a compromised error or event is triggered, then the current POSE of the fiducial marker array on one of the robots joints or links 102, 103 may be calculated by the robot forward kinematics and/or measured by the hardware/software that processes and receives data from the optical receivers 109 (Block 909). The hardware/software may then calculate a new solution for the robotic joints 102, 103 that may adjust the fiducial marker array 107 in a POSE that best matches the initially stored POSE (Block 911). The additional check (Block 913) may then be performed to determine if the fiducial marker array 107 is within the LOS of the optical receivers. Additionally or optionally, the hardware/software may also determine if the LOS is still compromised. If the LOS is not re-established or a compromised error still exists, then the procedure may be interrupted (Block 915). The robot 123 may then run through a series of joint solutions automatically such that the tool 106 may still perform the desired task on the target area. If the hardware/software re-establishes the LOS or the compromised error or event has been alleviated, then the robot joints/links 102, 103 at that joint solution is maintained. The coordinate transformation may then be updated and tracking resumed (Block 917).

It should be appreciated, that the initially stored orientation of the fiducial marker array 107 as a reference orientation may not need to be used (Block 901). An optional, combination or variation of the technique as described in FIG. 9 may be implemented with that of FIG. 8.

Distributed Fiducial Markers

Figure 10:
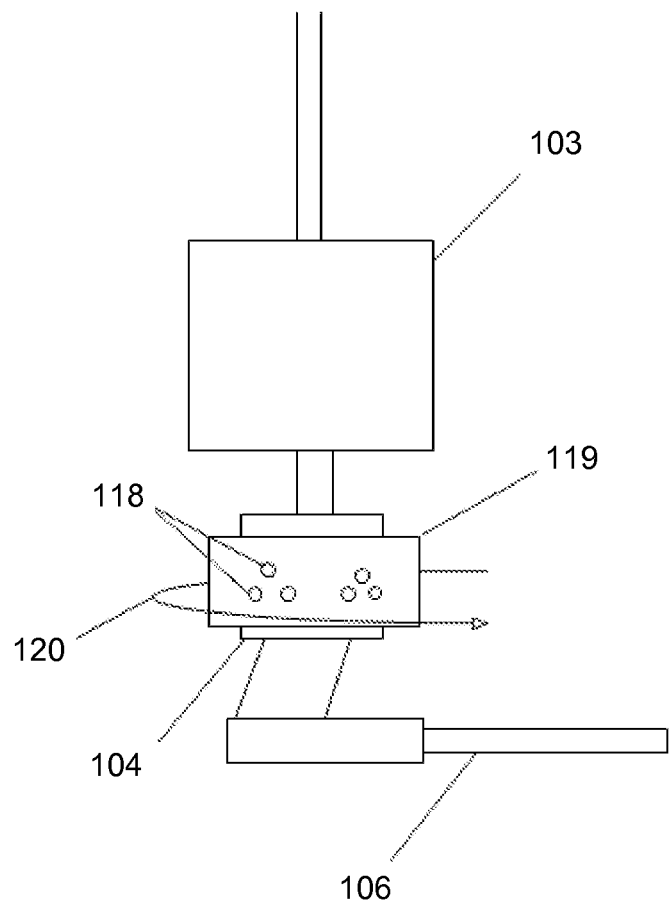
FIG. 10 illustratively shows a distribution of markers on a portion of the robot in accordance with embodiments of the invention.

In a particular inventive embodiment, fiducial markers may be directly attached to or incorporated with the tool 106, end effector flange 104, robot joints/links (102, 103), movable joints (119, 114, 116), and any combination thereof in a uniform distributed manner. For example, FIG. 10 illustrates a distribution of fiducial markers 118 on movable joint 119. The location of the fiducial markers 118 may be distributed in a known configuration (i.e., the distances between fiducial markers 118 and/or their locations on the movable joint 119) so when the robot articulates, the hardware/software or active movable joint controller may re-orient the movable joint 119 to maintain the LOS. It should be appreciated, that by adding additional fiducial markers in such a configuration, requires less rotation or articulation of the movable joint 119 to maintain LOS (i.e., the amount the movable joint 119 needs to rotate in degree of freedom 120 in this case is less because there are more makers).

Active Fiducial Marker Array with Hand-Held Surgical System

Figure 11:
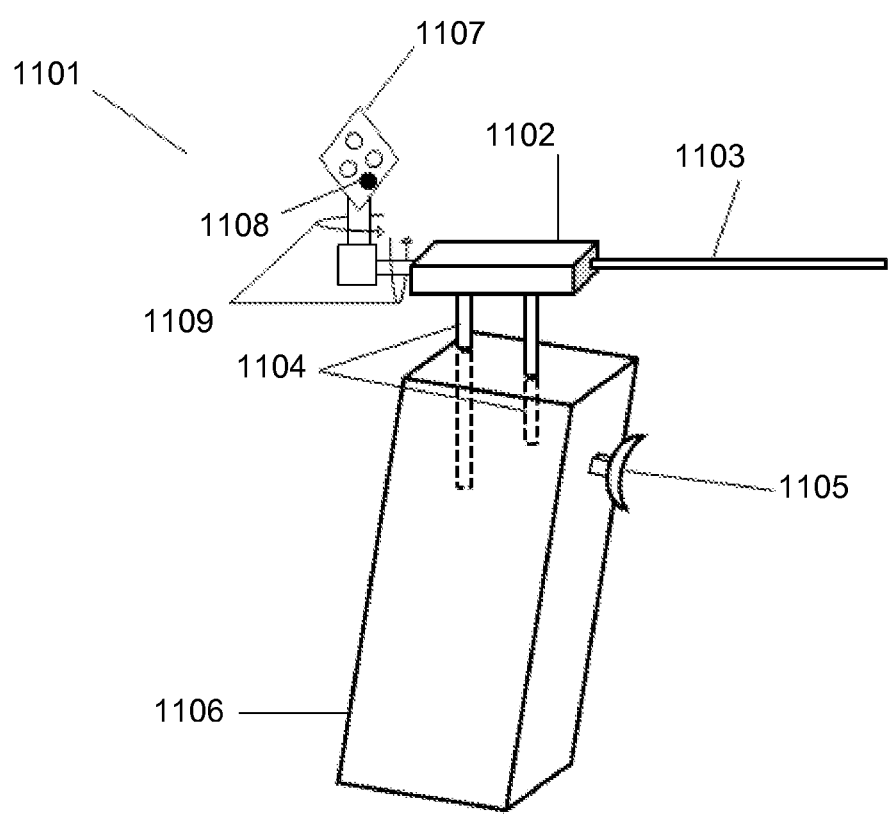
FIG. 11 illustratively shows a multiple degree of freedom active fiducial marker array utilized with a hand-held device in accordance with embodiments of the invention.

In specific inventive embodiments, with respect to FIG. 11, a hand-held articulating tool 1101 is shown. The hand-held articulating tool 1101 briefly includes a tool housing 1102, a tool 1103, a hand-held portion 1106, actuating components 1104 that may articulate/adjust the tool housing 1102 in at least two degrees of freedom, and an operator interactive mechanism 1105. A fiducial marker array 1107 may be positioned and oriented in at least one degree of freedom (indicated by arrows 1109) by way of articulating components similar to the movable joints (119, 114 and 116) as previously described. The fiducial marker array 1107 may similarly be re-positioned and/or re-oriented by one or a combination of the methods previously described.

The fiducial marker array 1107 may also include accelerometers and gyroscopes, collectively known as inertial measurement units (IMU) 1108 in addition to the fiducial markers. In one embodiment, an active controller and/or processor are incorporated within the active fiducial marker array 1107 and electrically or wirelessly connected to receive and read the measurements from the IMU 1108.

The hand-held device 1101 may be used to cut straight lines precisely by tracking the tool housing 1102 and utilizing the actuators to maintain a desired plane that has been pre-defined by the user. Once a cut is finished, the user may need to cut another plane in a different direction, for example, the drill may be flipped 180 degrees to make a new cut. However, the LOS between the fiducial marker array 1107 and the optical receivers 109 may be lost. The gyroscopes and/or accelerometers (IMU) 1108 may be used to measure a user's motion such that the hardware/software or active movable joint controller automatically re-orients and/or re-positions the fiducial marker array 1107 to counteract the user's motion to maintain LOS. In one embodiment, the accelerometer may be used to measure the direction of the floor and be used to aid in re-orienting the fiducial marker array 1107. In one inventive embodiment, once the LOS has been re-established or after the fiducial marker array 1107 has been re-positioned, the IMU(s) 1108 POSE may be re-set to reduce any errors that may have accumulated due to drift.

Active Fiducial Marker Array Attached to an Object Such as a Patient's Bone

In certain computer assisted surgical procedures, such as total knee arthroplasty, the bone may be optically tracked in space. However, the tracked bone may be articulated in a wide range of motion whereby the accuracy and/or visibility of the fiducial marker array may be lost or compromised. Therefore, in a specific inventive embodiment, with reference to FIG. 12, an active fiducial marker array 1206 may be attached to a patient's anatomy, illustratively shown here as a patient's knee 1201. The fiducial marker array 1206 may include two or more fiducial markers 1205. The fiducial marker array 1206 may contain an instrumented, motorized axis 1203 that keeps the fiducial marker array 1206 on the optimal viewing plane with respect to the optical receivers 109. The optimal viewing plane may be controlled by the hardware/software, an active motorized axis controller, and/or may be controlled directly by the fiducial marker array 1206.

The fiducial marker array 1206 may be attached to the bone via a joint 1204 and a bone fixation member 1202. The bone fixation member 1202 may be fastened to the bone 1201 using a fastening element illustratively including screws, clamps, and clasps. An articulating component, illustratively including a motor, stepper motor, servo motor, may provide the mechanism for articulating the movable joint 1204 and the attached fiducial marker array 1206. The fiducial marker array 1206 may also be articulated by a user. The movable joint 1204 may also include a position and/or rotation sensor such as an encoder to measure the position and/or angle of the fiducial marker array 1206 relative to the fixation member 1202. The fiducial marker array 1206, joint 1204 and/or fixation member 1202 may also include one or more accelerometers and or gyroscopes to provide local information about the POSE of the fiducial marker array 1206 (e.g., the direction of gravity).

To track the bone 1201, the fixation member 1202 may be attached to the bone 1201 with methods previously described. The fiducial marker array 1206 may be assembled or incorporated with the fixation member 1202 by way of one or more movable joints 1204. An initial calibration or registration technique may then be performed using techniques well known in the art such that the coordinates of the bone 1201 is known with respect to the coordinates of the fiducial marker array 1206 and the coordinates of the fiducial marker array 1206 is known with respect to the coordinates of the tracking system. An extra coordinate transformation may take into account the measured angle from the encoder values incorporated with the moveable joint 1204. The control of the movable joint 1204 and thus the fiducial marker array 1206 may be performed manually by a user or automatically actuated. If the fiducial marker array 1206 is automatically actuated, then the hardware/software, an active movable joint controller and/or local information (i.e., direction of gravity from an accelerometer) may determine the POSE of the fiducial marker array 1206. The hardware/software or active movable joint controller may control the POSE using information about visibility, accuracy, and/or POSE of the fiducial marker array relative to the optical receivers in the measuring volume of the tracking system.

If or when the fiducial marker array 1206 is actuated, the measured angle from the encoder values incorporated with the movable joint 1204 may then be transferred to the hardware/software or active movable joint controller either by direct wiring or wirelessly. Multiplication of the transformation matrix to fiducial marker array 1206 by the rotational transformation matrix given by the movable joint 1204 encoder may then provide the true transformation matrix to the tracked rigid body (e.g., a patient's knee 1201) with respect to the optical receivers 109.

Figure 13:
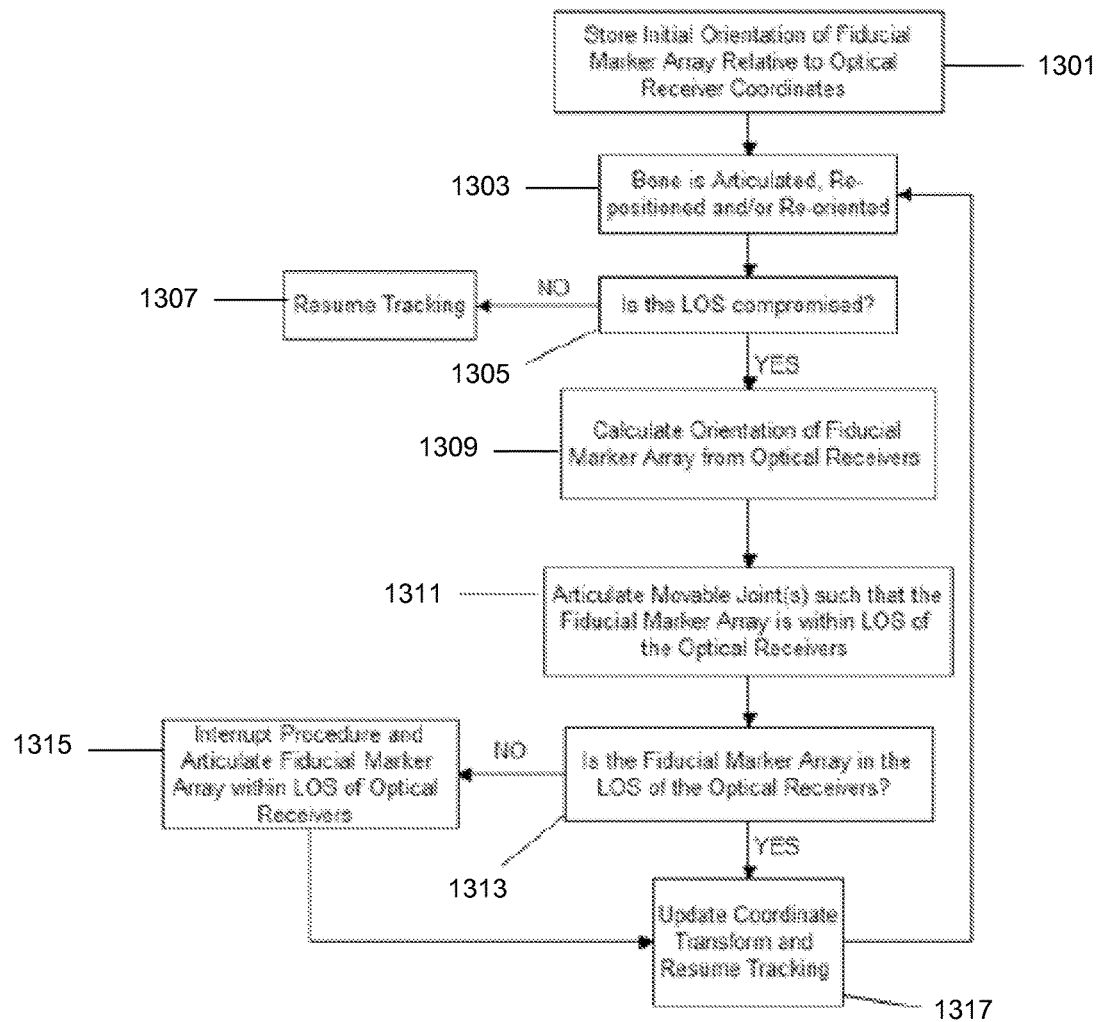
FIG. 13 is an illustrative flow chart of a method for actively articulating and monitoring a fiducial marker array attached to patient's bone relative to optical receiver coordinates in accordance with embodiments of the invention.

In a particular inventive embodiment, the fiducial marker array 1206 may have a control scheme as outlined in the flowchart shown in FIG. 13. An initial orientation of the fiducial marker array 1206, after calibration and registration may be stored in the hardware/software or an active movable joint controller (Block 1301). As the bone is articulated, re-oriented or re-positioned (Block 1303), the hardware/software processing and receiving data from the optical receivers may monitor the fiducial marker array 1206 to determine if the LOS or field of view may be or become compromised (Block 1305). A compromised event or error may be triggered by similar issues as previously described. If no such error or event occurs, then the tracking resumes (Block 1307). If, however, an event or error occurs, the POSE of the fiducial marker array may be calculated (Block 1309) from the hardware/software processing and receiving data from the optical receivers 109. The hardware/software or active movable joint controller may then calculate and send a joint command to the movable joint 1204 such that the fiducial marker array 1206 best matches the initially stored POSE (Block 1311). The additional LOS verification (Block 1313), procedure interruption (Block 1315), and coordinate transformation update (Block 1317) may then be or optionally implemented as previously described.

Figure 14:
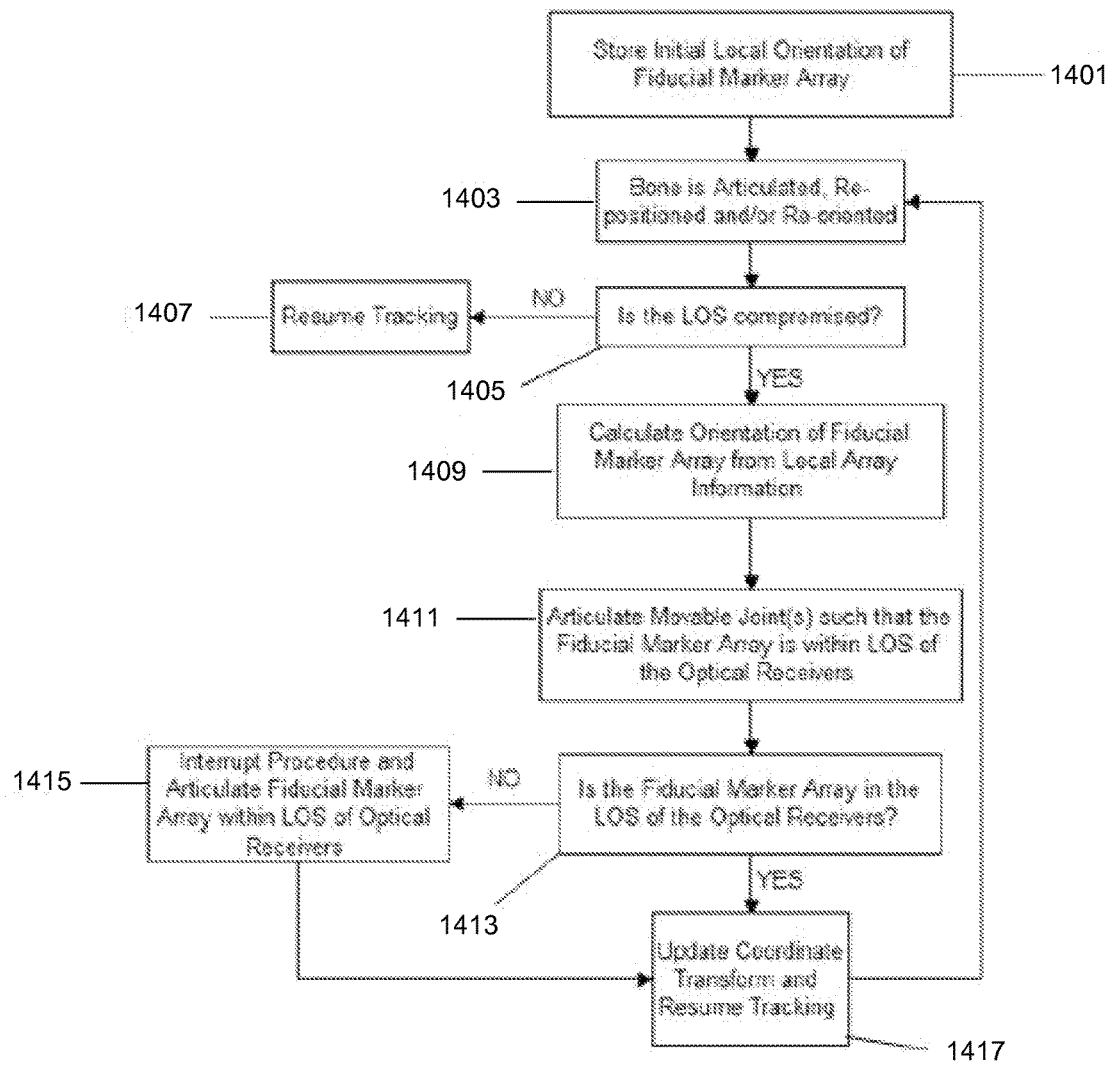
FIG. 14 is an illustrative flow chart of a method for actively articulating and monitoring a fiducial marker array attached to patient's bone relative to local array information in accordance with embodiments of the invention.

Similarly, with respect to the flowchart of FIG. 14, local information from the fiducial marker array 1206 may be initially stored, such as the direction of gravity relative to the initial orientation of the accelerometer (Block 1401). As the bone is articulated, re-positions or re-orients (Block 1403) the LOS may be monitored by the hardware/software or active movable joint controller to determine if a compromised error or event may occur (Block 1405). If no such error or event occurs, then the tracking resumes (Block 1407). If, however, an event or error occurs, then the orientation of the fiducial marker array 1206 may be determined by the local information, such as an accelerometer (Block 1409). The movable joint 1204 may then articulate (Block 1411) the fiducial marker array 1206 such that gravity vectors from the initially stored orientation and the current orientation is minimized. Therefore, the fiducial marker array 1206 may maintain or be optimized in the LOS of the optical receivers 109. The additional LOS verification (Block 1413), procedure interruption (Block 1315), and coordinate transformation update (Block 1417) may then be or optionally implemented as previously described.

Figure 15:
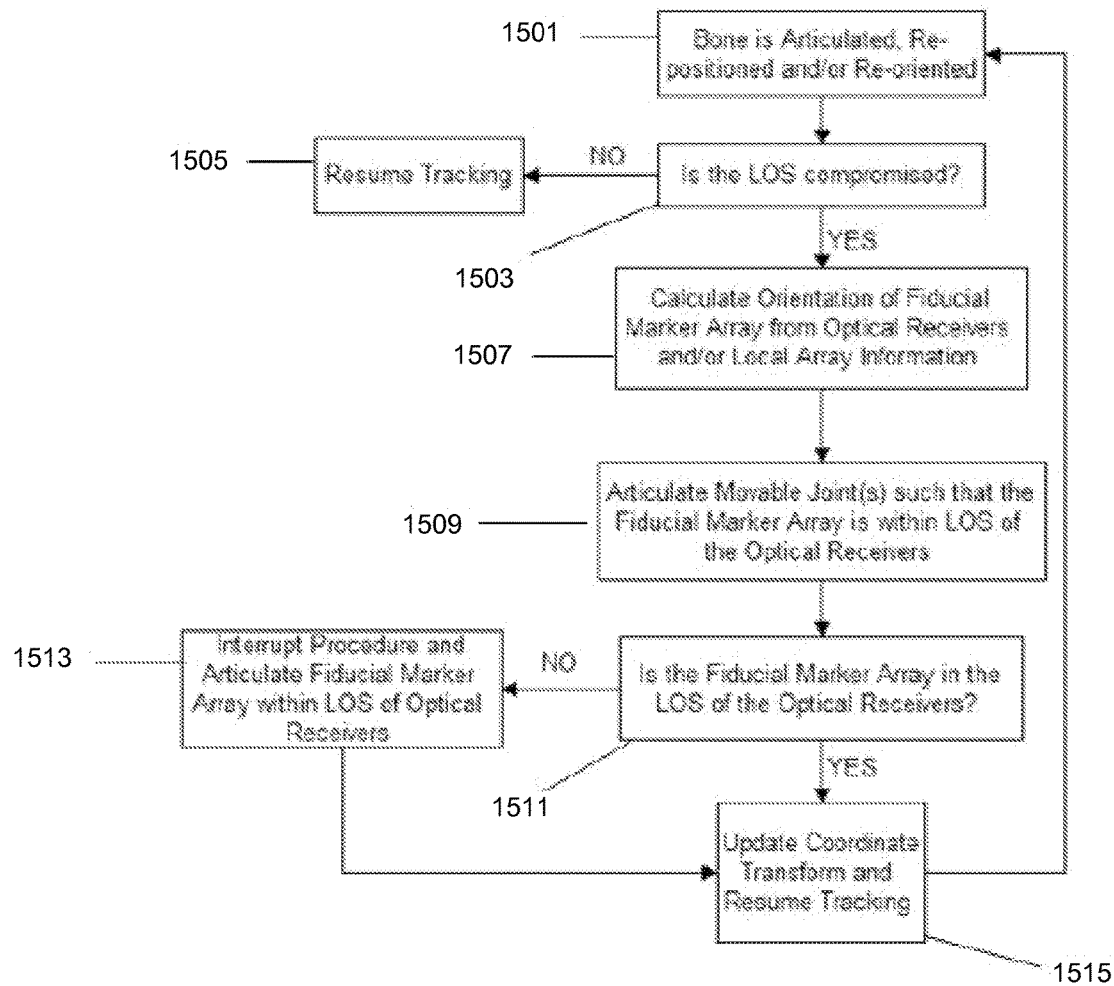
FIG. 15 is an illustrative flow chart of a method for actively articulating and monitoring a fiducial marker array attached to patient's bone without an initially stored reference orientation in accordance with embodiments of the invention.

Additionally, with reference to the flowchart of FIG. 15, the initially stored orientation may not be necessary as an orientation reference to re-establish or optimize the LOS. The reestablishing and optimizing of the LOS may very well be accomplished by the methods or variations of that as described in FIG. 8. In particular inventive embodiments, the LOS may be re-established or optimized without an initially stored POSE. The patient's bone may be articulated, repositioned, or reoriented in the field of view and LOS of the optical receivers (Block 1501), the hardware/software may monitor if the LOS may be or become compromised (Block 1503). For example, if the hardware/software determines the fiducial marker array 107 is approaching a boundary of the tracking field of view, then a compromised event or error may be triggered. Similarly, the compromised event may occur due to a poor orientation of the fiducial marker array 107 relative to the optical receivers 109. If no such event is triggered then the tracking resumes (Block 1505). If, however, a compromised event is triggered, then the current POSE of the fiducial marker array may be calculated either from the forward kinematics of the robot 123 or measured by the hardware/software processing and receiving data from the optical receivers 109 (Block 1507). Since the coordinate boundaries of the tracking field of view is known by the hardware/software, the hardware/software may send a joint command to the movable joint(s) 119, 114 and/or 116 to articulate the fiducial marker array 107 such that the LOS is re-established or optimized (Block 1509). The additional verification step (Block 1511), procedure interruption (Block 1513) and coordinate transform update (Block 1515) may then all or optionally be implemented as previously described.

The exceptions being that the POSE of the fiducial marker array 1206 may be calculated by the hardware/software processing and receiving data from the optical receivers 109 or the local information (i.e., accelerometer) associated with the fiducial marker array 1206, movable joint 1204 and/or fixation member 1202.

It should be appreciated that multi-faced arrays (i.e., a single fiducial marker array with different sets of fiducial markers that face different directions may be used to try and maintain or optimize the LOS. With the methods and techniques described, one could minimize the number of face changes, or optimize an active face selection at the beginning of a procedure. Furthermore, one could manage the robot motion to do face changes only during non-critical parts of a procedure, for example when the tool 106 is not operating.

Robot Positioning and Initial Optimal Fiducial Marker Array Placement

In a specific inventive embodiment, prior to tracking, the robot 123 may instruct the user to position and/or orient the tool 106 in an optimal location for a given procedure or depending on how the anatomy is positioned. The user may then adjust the robot base 105 and/or change the height of the tool 106 relative the robot base 105, such that the tool 106 is positioned and/or oriented as instructed. The instructions may be provided by for example, a monitor 111, a heads up display unit, Google Glass™, and the like. Once the user has confirmed the best POSE of the robot by modifying the robot base 105 and robot base height, the POSE of the fiducial marker array 107 may be set that will least likely cause a disruption in the LOS with the optical receivers 109.

Articulating Optical Receivers

The field of view of most tracking systems are limited and fixed in one location prior to a medical procedure. Due to the fixed position in the operating room, the tracked objects may very well move outside the tracking field of view. Also, as described above, the orientation of the fiducial marker array(s) (107, 1206) relative to the optical receivers 109 may affect the accuracy and visibility for tracking. Thus, by fixing the optical receivers 109 in one location throughout a medical procedure, the accuracy may be affected and the user may have to intervene to reestablish the LOS.

Figure 16:
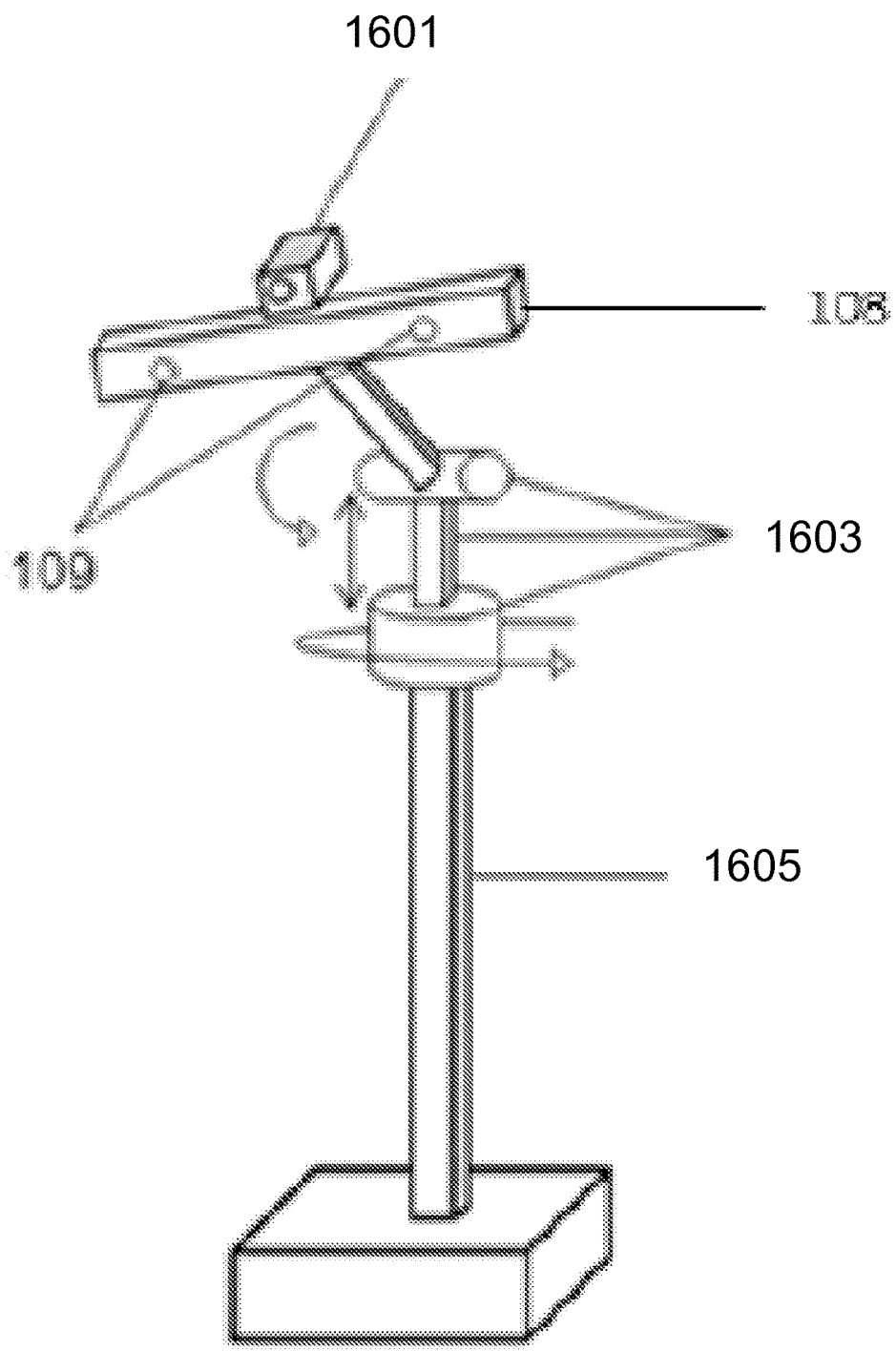
FIG. 16 depicts an actively controlled optical receiver stand for maintaining line of sight with fiducial marker arrays in accordance with embodiments of the invention.

Therefore, in a specific inventive embodiment, the hardware/software or an active optical receiver controller may instruct an optical receiver housing 108 to be re-positioned in a new location whereby the LOS may be maintained or the field of view is optimized. With respect to FIG. 16, the optical receivers 109 may be fixed relative to one another with a known geometry and enclosed in a housing 108. The housing 108 may be attached to a supporting structure 1605. However, it should be appreciated that the optical receivers 109 may also be positioned and relatively fixed at other locations that may include a surgical lamp, a light boom, on a particular wall, on the ceiling, on tracks and rails, and any combinations thereof. In this example, movable joint(s) 1603 may re-position and/or re-orient (illustratively shown by the arrows) the optical receiver housing 108 such that the optical receivers 109 are in a new POSE and the field of view may be changed. The movable joint(s) 1603 may similarly have position and/or rotation sensors such as encoders to measure the local POSE of the optical housing 108. The movable joint(s) 1603 may be articulated with articulating mechanisms illustratively including motors, stepper motors, servo motors, and the like. The movable joint(s) 1603 may be revolute, prismatic, and/or spherical. Additionally the movable joint(s) 1603 may be in communication with the hardware/software and/or a separate active movable joint controller that may be in communication with the hardware/software.

Figure 17:
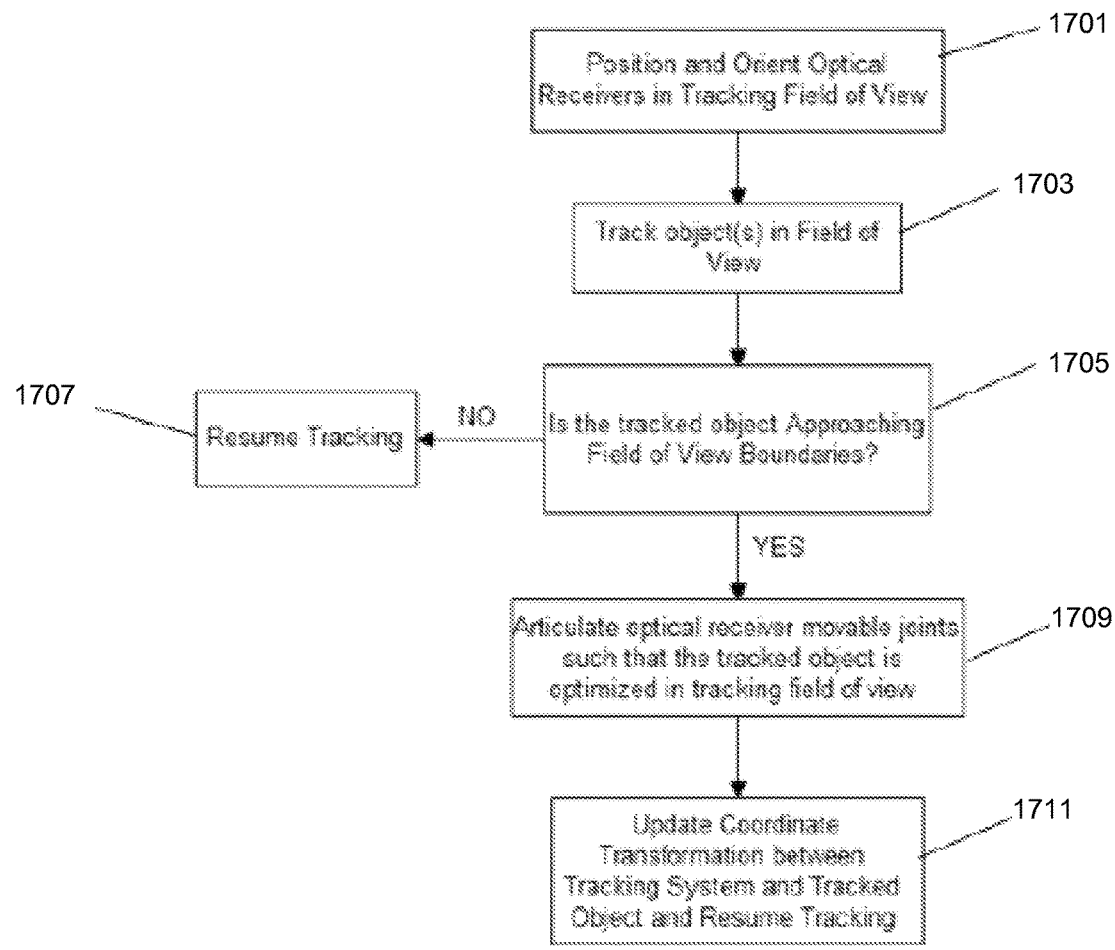
FIG. 17 is an illustrative flow chart of a method for actively articulating relatively fixed optical receivers to adjust the field of view in accordance with embodiments of the invention.

The movable joint(s) 1603 may automatically re-orient and/or re-position the optical receivers 109 such that the optical receivers 109 maintain the LOS with the fiducial marker array(s) (107, 1206) or optimizes the field of view. With respect to the flowchart in FIG. 17, the optical receivers 109 may be initially positioned and oriented in the tracking field of view (Block 1701). The coordinates between the fiducial marker array(s) (107, 1206) may then be calibrated or registered relative to the optical receiver coordinates using techniques well known in the art. The fiducial marker array(s) (107, 1206) may then be tracked (Block 1703) whereby the coordinate transforms between the fiducial marker array(s) (107, 1206) and optical receivers 109 may be constantly updated while the tracked objects move. The hardware/software or active movable joint controller may then monitor the tracked objects to determine if the LOS may be compromised and/or the field of view may be optimized. For example, if the tracked objects are approaching the field of view boundaries (Block 1705), the hardware/software or active movable joint controller may calculate and send joint commands to the movable joint(s) 1603 such that the LOS is re-established or the field of view is optimized (Block 1709). If the field of view is optimal or the LOS is maintained, then the tracking resumes (Block 1707). From the encoder values incorporated with the movable joint(s) 1603, the new position of the optical receivers 109 may be determined and the true coordinate transformation between the optical receivers 109 and the fiducial marker array(s) (107, 1206) may be calculated (Block 1711). Therefore, the tracking may go uninterrupted while maintaining the LOS and optimizing the field of view.

It should be appreciated, however, that when only the relative transformation of several fiducial marker arrays (i.e., 109, 1206 and any other tracked fiducial marker arrays) are needed, the actual position of the optical receivers is not important and the updated coordinate transform (Block 1711) may be neglected. However, when the absolute transformation of the fiducial marker arrays (e.g. 107 and 1206) with respect to the optical receivers 109 is needed, the updated coordinate transform may be calculated from the encoder values to find and track the absolute position of the fiducial marker arrays (e.g., 107 and 1206) with respect to the original position of the optical receivers 109.

In a particular inventive embodiment, machine vision may be utilized by way of a camera 1601 to survey the field of view that may be used with the hardware/software and/or active optical receiver controller to aid in controlling the movable joint(s) 1603 to re-position and/or re-orient the optical receivers 109. The machine vision may further be used with a light boom, surgical lamp and/or the mechanical stand to survey and/or define other objects within the operating theater. By defining or surveying the location of other objects in the room, the movable joints 1603 may be positioned and/or oriented around these object to maintain or optimize the LOS. For example, a surgeon's main light may be avoided by positioning and/or orienting the links in a different posture that still positions the optical receivers in an optimal location to see the fiducial marker arrays.

In the case of computer assisted surgery, a surgical workflow represented by various procedural stages may be exploited to optimize the field of view. The surgical workflow may illustratively include creating an initial surgical plan, calibrating the medical equipment routine, performing the actual procedure, and archiving the data post procedure. Therefore, in specific inventive embodiments, the optical receiver 109 movable joint(s) 1603 may automatically re-orient and/or re-position the optical receivers 109 based on a procedural step or instructions from a pre-surgical plan to focus on one or more specific fiducial marker arrays (e.g., 107 and 1206). For example, when one or fiducial marker arrays (e.g., 107 and 1206) are too far apart in the field of view, the optical receivers may be re-oriented and/or re-positioned to focus on the most critical set of fiducial markers for tracking.

Figure 18A:
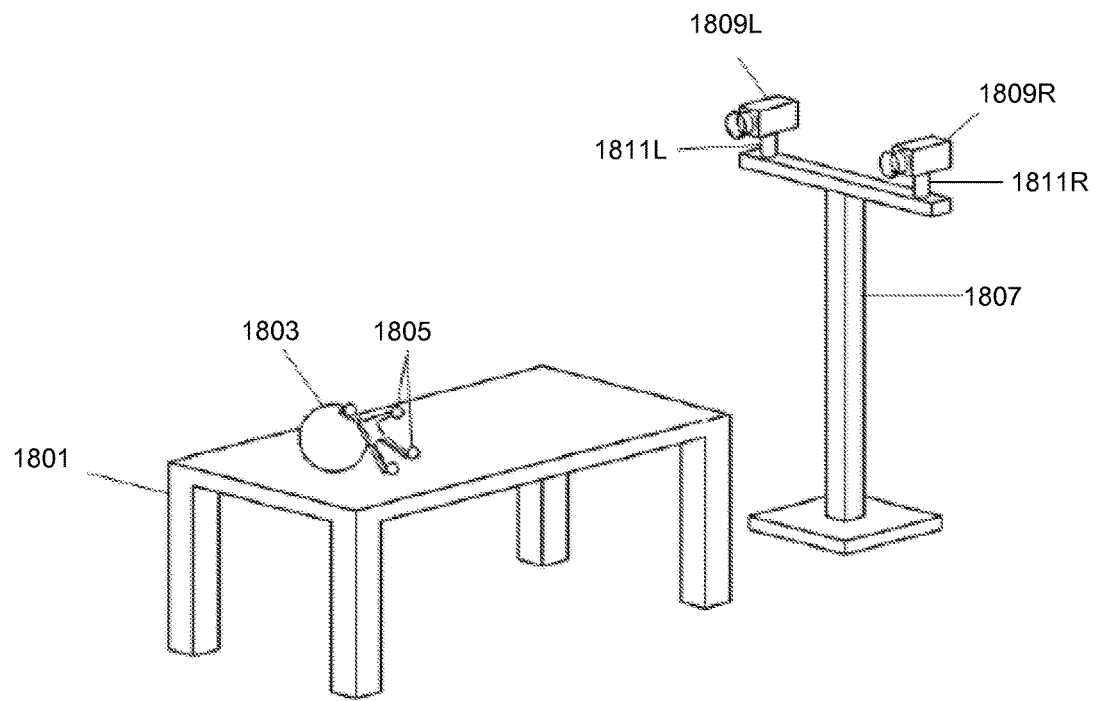
Figure 19:
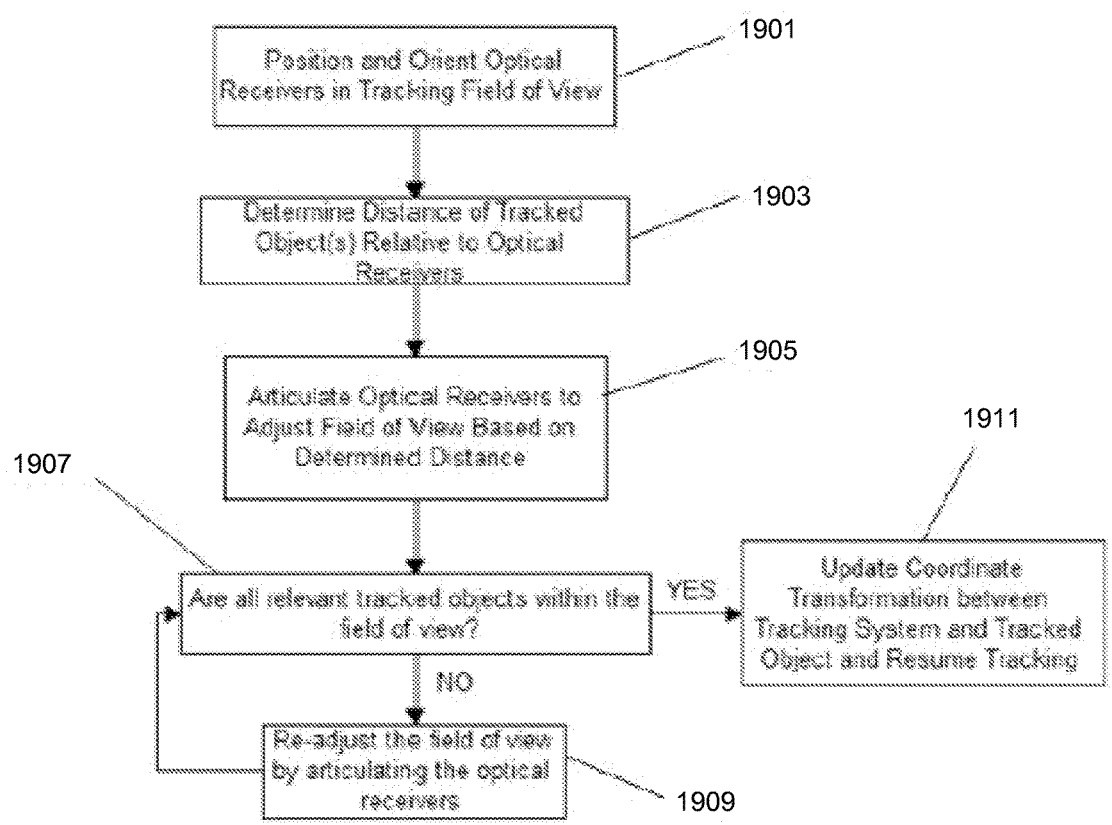
FIG. 19 is an illustrative flow chart of a method for articulating optical receivers independently to optimize the field of view in accordance with embodiments of the invention.

Additionally, current tracking systems are generally configured with the optical receivers 109 fixed relative to one another with a known geometry for accurate tracking. In general, a higher resolution and accuracy may be obtained by reducing the field of view. Smaller fields of view demand more precise positioning of the optical receivers 109 such that it is guaranteed all of the fiducial marker arrays (e.g., 107 and 1206) or other fiducial markers are observable. If the optical receivers 109 are fixed relative to one another and the ranges of motion of the fiducial marker arrays (e.g., 107 and 1206) in the operating theater are large, this might not be possible. Therefore, in a specific inventive embodiment, with respect to FIGS. 18A, 18B, and 18C, a left optical receiver 1809L and a right optical receiver 1809R may be connected to independent movable joints 1811L and 1811R respectively. As only two optical receivers 1809L and 1809R are shown, additional optical receivers may also be incorporated into the system. The movable joints 1811L and 1811R may be connected to or incorporated with a supporting structure 1807 such as a boom, a surgical light, or a mechanical stand. The movable joints 1811L and 1811R may articulate with articulating mechanisms illustratively including motors, stepper motors, servo motors, and the like. The movable joints 1811L and 1811R may be in communication with the hardware/software and/or a separate movable joint controller that may be in communication with the hardware/software. The movable joints 1811 and 1811R may further include one or more position and/or rotation sensors such as encoders to measure the local POSE of the optical receivers 1809L and 1809R. For illustrative purposes, a table 1801 is shown to provide a reference distance of an object 1803 to the optical receivers 1809L and 1809R. The object 1803 may have two or more fiducial markers 1805 attached thereto. The hardware/software or movable joint controller may control the movable joints 1811L and 1811R and optical receivers 1809R and 1809L by adjusting their respective angles independently. As the angle of the optical receivers 1809L and 1809R converge, the optical field of view is reduced and the accuracy of the system increases. Depending on the distance of the fiducial markers 1805 from the optical receivers 1809L and 1809R, an algorithm (discussed below in FIG. 19) may be used to calculate an optimum angle of the two optical receivers 1809L and 1809R, such that the highest accuracy within a desired field of view is achieved. For example, when a tracked object 1803 is close to the optical receivers 1809L and 1809R, the optical receiver 1809L and 1809R angles are more convergent as can be seen in FIG. 118C as compared to FIG. 18B.

The distance of the fiducial markers 1805 may be calculated using several different methods. In one exemplary embodiment, with reference to the flowchart of FIG. 19, the optical receivers may be initially positioned in the tracking field of view (Block 1901). In a particular inventive embodiment, the initial position may be determined automatically by the hardware/software or active movable controller. The optical receivers 1809L and 1809R may automatically rotate by way of the movable joints 1811L and 1811R, until the fiducial markers 1805 are detected and within the optical receivers 1809L and 1809R field of view. The distance of the fiducial markers 1805 from the optical receivers 1809L and 1809R may then be calculated by the hardware/software or active movable joint controller using standard techniques such as triangulation or time-of-flight (Block 1903). The distance may then be used with an algorithm to calculate an optimum angle for the optical receivers 1809L and 1809R such that the accuracy of tracking is optimal. The hardware/software or active movable joint controller may then send a joint command to articulate to the movable joints 1811L and 1811R, either independently and/or in unison based on the calculation (Block 1905). A verification step (Block 1907) by the hardware/software processing and received data from the optical receivers may determine if an optimal field of view has been obtained and all the tracked object(s) 1803 are in the field of view. The field of view may not be optimal due an incorrect measured distance. There also may be multiple tracked objects in the operating space whereby one object may be of the primary focus and the hardware/software optimized the field of view for the secondary object. Therefore, the hardware/software or active movable joint controller may re-articulate the movable joints 1811L and 1811R such that the field of view is optimized (Block 1909). Once the field of view is optimized, the coordinate transforms may be updated using the measured values from the encoders incorporated with the movable joints 1811L and 1811R (Block 1911).

In another example, a distance measurement sensor (not shown) may be attached to or incorporated with the optical receivers 1809L and 1809R. The distance measurement sensor may illustratively be a laser range finder, an acoustic sensor, proximity sensor, laser scanner, and the like. The distance measurement sensor may be used to collect the distance of the tracked object 1803 with respect to the optical receivers 1809L and 1809R. The distance of the tracked object 1803 determined by the distance measurement sensor may then be used with an algorithm to calculate the optimal angle for the optical receivers 1809L and 1809R. Additionally, the distance of the fiducial markers 1805 and/or the tracked object 1803 from the optical receivers 1809L and 1809R and/or the tracking system may be determined using a combination of a distance measurement sensor and the standard techniques (e.g., triangulation, time-of-flight) of the hardware/software.

The algorithm for determining the optimal angles of the optical receivers 1809L and 1809R may be constructed using experimental data or calibration techniques such as photogrammetric calibration or self-calibration. In one example, for a given tracking system configuration, an object or various objects are positioned at known distances and orientations from the optical receivers 1809L and 1809R. The optical receivers 1809L and 1809R are then rotated wherein the position and orientation of the tracked object(s) 1803 are recorded by the hardware/software. For a given rotation angle of the optical receivers 1809L and 1809R, an error may be calculated between the actual position of the tracked object(s) 1803 and the detected position and orientation recorded by the hardware/software. The distance of the object(s) 1803 with the least detected error for a given rotation angle may be considered the optimum angle for the optical receivers 1809L and 1809R. A curve may then be fitted for multiple optical receiver angles as a function of object distance. Therefore, once the distance of the object is determined as discussed above, the algorithm may update the optical receiver angles accordingly.

Furthermore, additional movable joints may be incorporated with and/or attached to the optical receivers 1809L and 1809R. For example, the distance between the two optical receivers 1809L and 1809R may be actuated, with a constant convergence angle, thus changing the convergence point and the shape of the field of view without changing the convergence angle. Additionally, a combination of both the distance between the two cameras and the angle between the two cameras may be actuated, thus allowing for changes in the convergence point and also the shape (i.e., change the workspace from being more cylindrical to more spherical) of the field of view by adjusting both or even more actuation mechanisms.

In one inventive embodiment, the optical receivers are attached with actuating mechanisms on a light boom. The actuating mechanisms on the light boom could similarly re-orient and/or re-position as a tracked marker gets close to the edge of the field of view to keep it inside. In another embodiment, the actuating mechanisms are part of the light boom. The light boom itself capable of re-orienting and/or re-positioning optical receivers located on the boom as a tracked marker gets close to the edge of the field of view to keep it inside. The light boom has one or more joints to control the re-positioning in at least one or more degrees of freedom. In a further embodiment, machine vision can be used with the light boom or the mechanical stand to survey or define other objects within the operating theater. By defining or surveying the location of other objects in the room, the joints and links of the mechanical stand or light boom can be positioned and/or oriented around these object as the LOS is trying to be maintained. For example, a surgeon's main light can be avoided by position and/or orienting the links in a different posture that still positions the optical receivers in an optimal location to see the tracking arrays.

Illustratively in a particular inventive embodiment, the optical receivers 1809L and 1809R (or more) may be attached with movable joints of a light boom. The movable joints may be part of or attached to the light boom. The movable joints of the light boom could similarly re-orient and/or re-position the optical receivers 1809L and 1809R, either independently or in unison, as a fiducial marker array (107, 1206) approaches a boundary of the field of view. Similarly, the light boom itself may be capable of re-orienting and/or re-positioning optical receivers 1809L and 1809R located on the boom as a fiducial marker array (107, 1206) approaches the boundary of the tracking field of view.

Targeted Visible Light Communication

It should be appreciated that the communication between the various components of the system may be accomplished using visible light communication (VLC) as disclosed in U.S. Provisional Patent Application Nos. 62/083,052 and 62/111,016. The various components described herein may include actuating light emitting diodes (LEDs) and LED data optical receivers to transmit and/or receive data. For example, the actuated LEDs may be incorporated, attached or in communication with the hardware/software, active movable joint controller, optical receivers (109, 1809L, 1809R), fiducial marker arrays (107, 1206), joints/links of a robot (102, 103), movable joints (119, 114, 116, 1204, 1603, 1811L, 1811R), any additional components of the system (i.e., additional fiducial marker arrays in the operating room, additional movable joints in mechanical communication with the fiducial marker arrays and/or optical receivers), and any combination thereof. It should also be appreciated that if the fiducial markers are active LEDs for tracking, the fiducial markers themselves may be actuated to transmit data.

Figure 12:
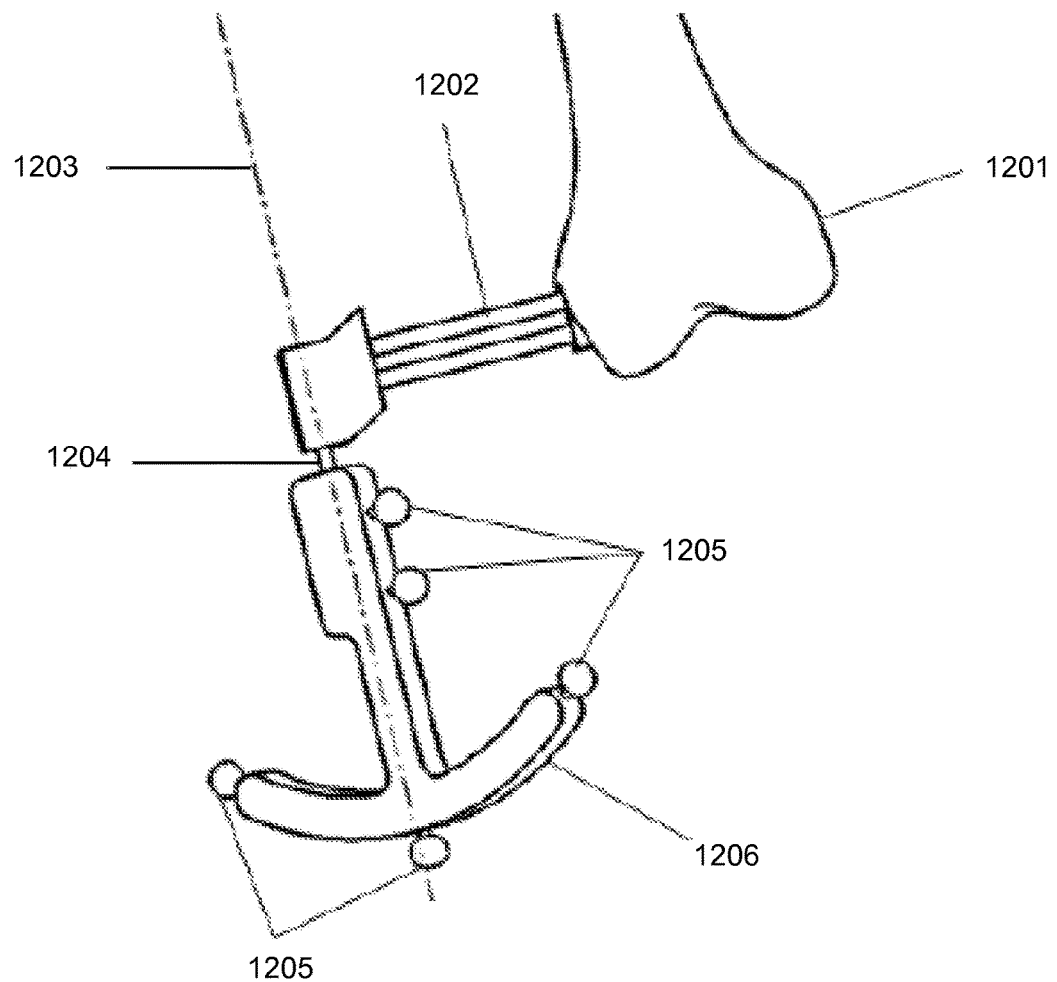
FIG. 12 illustratively depicts an active fiducial marker array attached to a patient's bone in accordance with embodiments of the invention.

The data transmitted and/or received by the actuated LEDs and LED optical receivers may include the joint commands to the movable joints to re-orient and/or re-position the fiducial marker arrays (107, 1206). The data transmitted and/or received may include the joint angles measure by the encoder values incorporated with the movable joints (119, 114, 116, 1204, 1603, 1811L, 1811R), to update the coordinate transformations for accurate tracking of the object(s). As an example, which may be utilized by any of the embodiments as previously described, an actuating LED for transmitting data and/or an LED optical receiver may be attached or incorporated with fiducial marker array 1206 as shown in FIG. 12. An actuating LED controller may be housed, attached or incorporated with the fixation member 1202, movable joint 1204 and/or fiducial marker array 1206, for processing data received by the LED optical receiver and/or controlling data sent by actuating the LEDs. The hardware/software or active movable joint controller may similarly be capable of receiving and transmitting data via actuated LEDs and LED optical receivers attached to and/or incorporated with any other components within the operating room. For example, another actuating LED and/or LED optical receiver in communication with the hardware/software or active movable joint controller may be illustratively attached, located, or incorporated with the optical receivers (109, 1809L, 1809R), a surgical lamp, a structural support (122, 1807), an optical receiver housing 108, the ceiling of the OR, a particular wall in the OR, or a VLC hub within the OR. In another inventive embodiment, the optical receivers 109 are stationed on a track or rails and positioned prior to surgery in a location whereby the LOS is most likely to be maintained.

The data transmitted to the optical receivers via the LED may instruct the optical receivers to be re-positioned in a new location whereby the LOS may be maintained more frequently. In one embodiment the optical receivers 109 are enclosed in a casing as shown in FIG. 1. The casing can be controllable by components to re-position and/or re-orient the optical receivers 109 in a new position as instructed by the LEDs on the tracking array 107.

If the hardware/software detect that a fiducial marker array 1206 may be approaching the boundary of the field of view, then the hardware/software or active movable joint controller may transmit a signal, by actuating the LEDs, to the LED optical receiver located on the fiducial marker array 1206. The signal may be a joint command to the movable joint 1204 to re-orient and/or re-position the fiducial marker array 1206 to optimize the field of view or LOS with the optical receivers (109, 1809L and/or 1809R). The actuated LEDs located on the fiducial marker 1206 may then transmit a signal, by actuating the LEDs, back to the hardware/software or active movable joint controller with the new POSE of the fiducial marker array 1206 measured by the encoder values incorporated therewith. The hardware/software or active movable joint controller may then update the coordinate transform accordingly to resume accurate tracking of the patient's knee 1201. The visible light communication may also be utilized to re-orient and/or re-position the optical receivers (109, 1809L, 1809R) or and optical receiver housing 108 to optimize the field of view, LOS or to maintain the LOS.

For example, at a known specific point during an operation, the robot may need to re-orient the end effector 180 degrees to complete a procedure. Illustratively, in total knee arthroplasty, the robot may be positioned in one direction to prepare the femur and then completely re-oriented to prepare the tibia to receive a knee implant. The processor can actuate the LEDs at this transition period to send data to the optical receivers to be re-positioned on the other side of the room whereby the new position of the optical receivers is most likely to maintain the LOS. Therefore the user does not have to manually adjust the optical receivers 109 and the likelihood of continuously maintaining the LOS between the markers and the tracking array is accomplished.

As but one example has been described, it should be appreciated that VLC may be used to transmit and/or receive data for multiple applications in accordance with the embodiments of the invention as described herein. It should also be appreciated that the fiducial marker arrays may include LEDs for VLC wherein VLC may require LOS. Thus, with the embodiments described herein, it is also contemplated that the LOS and/or field of view may be maintained and/or optimized for VLC.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A system comprising:
   a fiducial marker array;
   an optical tracking system with one or more optical receivers configured for line of sight (LOS) communication with said fiducial marker array;
   a robot comprising an end effector, a plurality of links and joints, and the fiducial marker array, wherein the end-effector is articulated by the plurality of links and joints;
   one or more movable joints in mechanical communication with said fiducial marker array said one or more movable joints provide degrees of freedom of movement to articulate said fiducial marker array independent of how the end-effector is articulated by the plurality of links and joint; and
   one or more controllers configured to actuate said one or more movable joints to cause the fiducial marker array to move relative to the end-effector in order to maintain LOS between said fiducial marker array and said one or more optical receivers.

2. The system of claim 1 wherein said fiducial marker array comprises a plurality of markers, where each marker of said plurality of markers is an individual optical emitter or reflector.

3. The system of claim 1 wherein said one or more movable joints are in mechanical communication with the robot.

4. The system of claim 1 wherein said one or more movable joints are incorporated with an end of an effector flange.

5. The system of claim 1 wherein said fiducial marker array further comprises an inertial measurement units (IMU).

6. The system of claim 1 wherein said robot is a hand-held robot.

7. The system of claim 1 wherein said one or more moveable joints further comprise one or more encoders to measure positions and orientations of said one or more moveable joints.

8. The system of claim 1 wherein said fiducial marker array further comprises emitting light emitting diode (LED)

markers, said emitting LED markers actuated by a processor to transmit data to said one or more optical receivers.

9. The system of claim 1 wherein kinematics define a position and a location of the end effector during movement of said robot; and wherein kinematics are used with said one or more controllers controlling the one or more movable joints to re-locate the fiducial marker array.

10. A process of using the system of claim 1 to maintain a line of sight (LOS) between said fiducial marker array and said one or more optical receivers, said process comprising:

positioning said one or more optical receivers in an initial location that minimizes LOS disruption within said system;

positioning said fiducial marker array manually or with said one or more movable joints to an initial position and orientation (POSE) that optimizes said fiducial marker array within a field of view of said one or more optical receivers;

recording an initial POSE of said fiducial marker array;

calculating a change in the POSE of said fiducial marker array;

determining a difference between the calculated change in the POSE and the initial POSE of said fiducial marker array; and articulating said one or more movable joints based on said determining to re-orient said fiducial marker array relative to the end-effector to maintain the LOS independent of a position or orientation of the end-effector.

11. The process of claim 10 wherein the calculating of the change in the POSE is based on forward kinematics.

12. The process of claim 11 wherein the forward kinematics are determined with a set encoder values incorporated with said one or more movable joints.

13. The process of claim 10 wherein said one or more controllers are configured to actuate said one or more movable joints to maintain LOS between said fiducial marker array and said one or more optical receivers.

14. The process of claim 10 wherein said fiducial marker array further comprises emitting light emitting diode (LED) markers, said emitting LED markers actuated by a processor to transmit data to said one or more optical receivers.

15. The process of claim 10 wherein the calculating of the change in the POSE is based on forward kinematics, where the forward kinematics define a position and a location of the end effector during movement of said robot and the forward kinematics are used with said one or more controllers controlling the one or more movable joints to re-locate the fiducial marker array.

* * * * *